(12) United States Patent
Inoue et al.

(10) Patent No.: US 8,283,163 B2
(45) Date of Patent: Oct. 9, 2012

(54) METHOD FOR PRODUCTION OF DENDRITIC CELL

(75) Inventors: Makoto Inoue, Ibaraki (JP); Mamoru Hasegawa, Ibaraki (JP); Yoshikazu Yonemitsu, Chiba (JP); Yui Harada, Saitama (JP)

(73) Assignees: DNAVEC Corporation, Ibaraki (JP); Yasuji Ueda, Ibaraki (JP)

(*) Notice: Subject to any disclaimer, the term of this patent is extended or adjusted under 35 U.S.C. 154(b) by 0 days.

(21) Appl. No.: 12/600,103

(22) PCT Filed: May 12, 2008

(86) PCT No.: PCT/JP2008/058719
§ 371 (c)(1),
(2), (4) Date: Mar. 10, 2010

(87) PCT Pub. No.: WO2008/143047
PCT Pub. Date: Nov. 27, 2008

(65) Prior Publication Data
US 2010/0184214 A1    Jul. 22, 2010

(30) Foreign Application Priority Data

May 17, 2007 (JP) ................................ 2007-132204

(51) Int. Cl.
*C12N 5/071* (2010.01)
*C12N 5/02* (2006.01)
(52) U.S. Cl. ....................................... 435/366; 435/377
(58) Field of Classification Search .................. None
See application file for complete search history.

(56) References Cited

U.S. PATENT DOCUMENTS

| | | | |
|---|---|---|---|
| 5,811,297 A | 9/1998 | Gopal | |
| 7,771,998 B2 | 8/2010 | Kirkin et al. | |
| 7,955,852 B2* | 6/2011 | Peled et al. | 435/377 |
| 8,093,049 B2* | 1/2012 | Tseng et al. | 435/377 |
| 2007/0269414 A1 | 11/2007 | Okano et al. | |
| 2008/0014183 A1 | 1/2008 | Okano et al. | |

FOREIGN PATENT DOCUMENTS

| | | |
|---|---|---|
| JP | 2000-508885 A | 7/2000 |
| JP | 2005-515192 A | 5/2005 |
| WO | WO 98/01538 A1 | 1/1998 |
| WO | WO 2005/042737 A1 | 5/2005 |
| WO | WO 2006/001122 A1 | 1/2006 |

OTHER PUBLICATIONS

Szabolcs et al (The Journal of Immunology. 1995; 154: 5851-5861).*
Bontkes et al. (J. Leukoc. Biol. 2002; 72: 321-329).*
Saraya et al. (British Journal of Haematology. 1996; 93(2): 258-164).*
English Language Translation of the International Preliminary Report on Patentability for International Application PCT/JP2008/058719, mailed Dec. 3, 2009.
Banchereau and Steinman, "Dendritic Cells and the Control of Immunity," *Nature* 19:392(6673):245-252, 1998.
Bontkes et al., "Expansion of Dendritic Cell Precursors from Human CD34+ Progenitor Cells Isolated from Healthy Donor Blood; Growth Factor Combination Determines Proliferation Rate and Functional Outcome," *J. Leukoc. Biol.* 72(2):321-329, 2002.
International Search Report for International Application No. PCT/JP2008/058719, mailed Jul. 22, 2008.
Kobari et al., "Ex Vivo Expansion Does Not Alter the Capacity of Umbilical Cord Blood CD34+ Cells to Generate Functional T Lymphocytes and Dendritic Cells." *Stem Cells* 24(9):2150-2157, 2006.
Saraya and Reid, "Synergistic Interaction Between c-kit Ligand (SCF), GM-CSF and TNF Promotes Optimal Dendritic Langerhans Cell Proliferation from Primitive Progenitors in Human Bone Marrow," *Adv. Exp. Med. Biol.* 378:13-16, 1995.
Sato et al., "Generation of Dendritic Cells from Fresh and Frozen Cord Blood CD34+ Cells," *Cyrobiology* 37(4):362-371, 1998.
Shibata et al., "Induction of Efficient Antitumor Immunity Using Dendritic Cells Activated by Recombinant Sendai Virus and its Modulation by Exogenous IFN-βGene," *J. Immunol.* 177(6)3564-3576, 2006.
Steinman, "The Dendritic Cell System and its Role in Immunogenicity," *Annu. Rev. Immunol.* 9:271-296, 1991.
Szabolcs et al., "Expansion of Immunostimulatory Dendritic Cells Among the Myeloid Progeny of Human CD34+ Bone Marrow Precursors Cultured with c-kit Ligand, Granulocyte-Macrophage Colony-Stimulating Factor, and TNF-α," *J. Immunol.* 154(11):5851-5861, 1995.
Ueda et al., "Expansion of Human NOD/SCID-Repopulating Cells by Stem Cell Factor, Flk2/Flt3 Ligand, Thrombopoietin, IL-6, and Soluble IL-6 Receptor," *J. Clin. Invest.* 105(7)1013-1021, 2000.
Yoneyama et al., "Development of Immunostimulatory Virotherapy Using Non-transmissible Sendai Virus-Activated Dendritic Cells," *Biochem. Biophys. Res. Commun.* 355(1):129-135, 2007; Epub, Feb. 2, 2007.
Coulon et al., "In Vitro Production of Human Antigen Presenting Cells Issued from Bone Marrow of Patients with Cancer," *Hematology and Cell Therapy* 39(5): 237-244 (1997).
Harada et al., "Cytokine-Based Log-Scale Expansion of Functional Human Dendritic Cells," *Mol. Ther.* 17(Supplement 1): S220 (May 2009). (Abstract 576).
Supplementary European Search Report for European Patent Application No. EP 08 75 2599, completed May 26, 2011, mailed Jun. 8, 2011.
Xu et al., "Implication of Delayed TNF-α Exposure on Dendritic Cell Maturation and Expansion from Cryopreserved Cord Blood CD34+ Hematopoietic Progenitors," *J. Immunol. Methods* 293(1-2): 169-182 (2004).
U.S. Appl. No. 13/127,753 titled "Method for Producing Dendritic Cells," filed May 5, 2011.

(Continued)

*Primary Examiner* — Scott Long
(74) *Attorney, Agent, or Firm* — Clark & Elbing LLP

(57) ABSTRACT

The present invention provides methods for producing DCs, which comprise the step of culturing DC precursor cells in the presence of multiple cytokines, dendritic cells produced thereby, and uses thereof. The methods of the present invention enable production of large quantities of DC precursors with a high ability to differentiate into DCs. The present invention enables one to obtain large quantities of DCs from a small number of DC precursor cells, and therefore makes it easier to increase the number of DCs for administration in DC-based anti-tumor immunotherapy, treatment of infection, and such. Thus, an enhancement is expected for the effect of DC vaccines.

8 Claims, 30 Drawing Sheets

OTHER PUBLICATIONS

Bernhard et al. "Generation of immunostimulatory dendritic cells from human CD34+ hematopoietic progenitor cells of the bone marrow and peripheral blood," *Cancer Research* 55:1099-1104 (1995).

Fisch et al., "Generation of antigen-presenting cells for soluble protein antigens ex vivo from peripheral blood CD34+ hematopoietic progenitor cells in cancer patients," *Eur. J. Immunol.* 26:595-600 (1996).

Siena et al., "Massive ex vivo generation of functional dendritic cells from mobilized CD34+ blood progenitors for anticancer therapy," *Experimental Hematology* 23:1463-1471 (1995).

"Cytokines" Mire-Sluis and Thorpe, Eds., Academic Press, Front cover, bibliographic page, and pp. 38-39 (4 pages), 1998.

Ward et al., "Pathology of Immunodeficient Mice With Naturally Occurring Murine Norovirus Infection," *Toxicologic Pathology* 34(6):708-715 (2006).

Vital et al., "The Sensitizers Nickel Sulfate and 2,4-dinitrofluorobenzene Increase CD40 and IL-12 Receptor Expression in a Fetal Skin Dendritic Cell Line," *Bioscience Reports* 24(3):191-202 (2005).

\* cited by examiner (A)

(B)

METHOD FOR PRODUCTION OF DENDRITIC CELL

CROSS-REFERENCE TO RELATED APPLICATIONS

The present application is the U.S. National Stage of PCT/JP2008/058719, filed May 12, 2008, which claims the benefit of Japanese Patent Application Serial No. JP 2007-132204, filed May 17, 2007.

TECHNICAL FIELD

The present invention relates to methods for producing dendritic cells, produced dendritic cells, and uses thereof.

BACKGROUND ART

Dendritic cells (DCs) are antigen-presenting cells (APCs) present in peripheral blood, skin, lymphatic organs, and thymus, and are widely distributed in lymphatic and non-lymphatic tissues (see Steinman, R. M. Ann. Rev. Immunol. 9:271 (1991); Banchereau, J. B. and R. M. Steinman, Nature 392:245 (1998)). Dendritic cells have strong antigen-presenting ability and express antigenic peptides on MHC class I and II on the dendritic cell surface, which activate CD4 and CD8 T cells, respectively. Through this activation, they induce an in vivo immune response against specific antigens (e.g., antigens of pathogenic microorganisms, tumor-related antigens, and transplantation antigens).

The strong ability of DC to induce immunity is useful in immunotherapy (DC therapy) against many tumors. The present inventors have previously demonstrated that DCs stimulated with Sendai virus (SeV) have a strong anti-tumor effect in mice (S. Shibata et al., J. Immunol, 177: 3564-3576 (2006); Yoneyama, Y. et al., Biochem. Biophys. Res. Commun., 355:129-135 (2007)). The anti-tumor effect depends on the number of inoculated DCs. Clinically, the number of inoculated DCs is also thought to have a great influence on the therapeutic effect. However, there may be many cases where only a limited number of DC precursor cells (DC progenitors) can be collected due to the patient's condition. As a result, there is a possibility that the therapeutic effect may become insufficient due to insufficient number of DCs obtained. Thus, there is a demand for methods that efficiently expand limited DC precursor cells.

[Non-Patent Document 1] Steinman, R. M., 1991, Ann. Rev. Immunol. 9: 271-296.
[Non-Patent Document 2] Banchereau, J. B. and R. M. Steinman, 1998, Nature 392: 245-252.
[Non-Patent Document 3] Shibata, S. et al., J. Immunol, 2006 177: 3564-3576.
[Non-Patent Document 4] Yoneyama, Y. et al., Biochem. Biophys. Res. Commun., 2007, 355:129-135.

DISCLOSURE OF THE INVENTION

Problems to be Solved by the Invention

The present invention was achieved in view of the above circumstances. An objective of the present invention is to provide methods for efficiently producing large quantities of dendritic cells.

Means for Solving the Problems

In order to develop methods for efficiently expanding DC precursor cells and differentiating them into DCs, the present inventors cultured DC precursor cells for varying periods of time in the presence of various cytokines. Then, following DC differentiation, the expanded cells were analyzed using DC surface markers as an indicator. As a result, the present inventors discovered that DC precursor cells proliferate markedly when cultured in media containing stem cell factor (SCF) and interleukin (IL)-3. Furthermore, DC precursor cells proliferated more markedly when cultured in media supplemented with Flt-3 ligand and IL-6 in addition to SCF and IL-3 (i.e., containing Flt-3 ligand, SCF, IL-3, and IL-6 (abbreviated as FS36)). The number of DCs obtained was several hundred times higher by differentiation of the expanded cells using GM-CSF and IL-4, or GM-CSF and SCF than by differentiation carried out immediately after collection. In particular, the cell population that was differentiated after about three weeks of culture with FS36 had a significantly high proportion of DCs. This revealed that culturing with FS36 for about three weeks is an excellent method for expanding DCs. Like DCs obtained by conventional differentiation methods, cells obtained after expansion were confirmed to show enhanced expression of the co-stimulatory molecules CD80 and CD86 when infected with RNA virus or treated with LPS or such. Furthermore, DCs were also found to markedly proliferate by culturing human $CD34^+$ cells in a medium containing GM-CSF and SCF. Likewise, the obtained DCs were confirmed to display enhanced expression of CD86 when treated with LPS. Thus, the present invention provides methods for expanding DC precursor cells in large quantities, and methods for efficiently differentiating the obtained DC precursor cells into DCs. DCs produced by these methods are useful in immunotherapy against cancer, infection, or such.

Specifically, the present invention relates to methods for producing dendritic cells, the produced dendritic cells, uses thereof, and the like. More specifically, the present invention relates to:

[1] a method for producing a dendritic cell, wherein the method comprises the step of culturing a dendritic cell precursor cell in the presence of a plurality of cytokines;

[2] the method of [1], wherein the plurality of cytokines are granulocyte/macrophage colony stimulating factor (GM-CSF) and stem cell factor (SCF);

[3] the method of [1] or [2], wherein the dendritic cell precursor cell is a cell derived from human;

[4] the method of [2] or [3], wherein the step is a step of culturing a dendritic cell precursor cell in the presence of 1 ng/ml or higher concentration of GM-CSF and 0.5 ng/ml or higher concentration of SCF;

[5] the method of [4], wherein the step is a step of culturing a dendritic cell precursor cell in the presence of 10 ng/ml or higher concentration of GM-CSF and 5 ng/ml or higher concentration of SCF;

[6] the method of [4], wherein the step is a step of culturing DC precursor cells in the presence of 1 ng/ml to 100 ng/ml GM-CSF and 0.5 ng/ml to 50 ng/ml SCF; and

[7] the method of [5] or [6], wherein the step is a step of culturing a dendritic cell precursor cell in the presence of 10 ng/ml to 100 ng/ml GM-CSF and 5 ng/ml to 50 ng/ml SCF.

It is intended that in each of the items described above, inventions comprising any combination of two or more inventions described in each item that cites the same item are also included in the antecedent items that they cite. Furthermore, it is intended that any inventions described herein and any combinations thereof are also included in the present invention. In addition, it is intended that any inventions excluding any elements described herein or any combinations thereof are also included in the present invention. Herein, for example, when a specific embodiment is stated as "preferable", the specification discloses not only the embodiment itself, but also inventions that exclude the embodiment from the disclosed antecedent inventions that comprise the embodiment.

Effects of the Invention

Dendritic cells have a strong ability to induce immunity. Thus, dendritic cells obtained by the methods of the present invention are useful as dendritic cell (DC) vaccine which is useful in immunotherapy for cancer, infection, and such. For example, in tumor immunotherapy, dendritic cells are made to present tumor antigens by mixing dendritic cells with tumor cell lysates, pulsing dendritic cells with peptides, introducing tumor antigen genes into dendritic cells, or such; and the dendritic cells can be used in DC therapy against tumors. Even when the quantity of DCs collected from a patient is small, sufficient number of DCs to produce therapeutic effect can be prepared by using the methods of the present invention.

BRIEF DESCRIPTION OF THE DRAWINGS

Scales of the vertical axis of the graphs in FIGS. 1, 2, 4 to 10, 13, 15, 21(A), 21(B), 22(A), 28, and 29, which are described below, indicate the following.

1.E+04, 1e4, or 1.00E+04: $1.0 \times 10^4$ (cells)
1.E+05 or 1.00E+05: $1.0 \times 10^5$ (cells)
1.E+06 or 1.00E+06: $1.0 \times 10^6$ (cells)
1.E+07 or 1.00E+07: $1.0 \times 10^7$ (cells)
1.E+08 or 1.00E+08: $1.0 \times 10^8$ (cells)
1.E+09 or 1.00E+09: $1.0 \times 10^9$ (cells)
1.E+10 or 1.00E+10: $1.0 \times 10^{10}$ (cells)
1.E+11 or 1.00E+11: $1.0 \times 10^{11}$ (cells)
1.E+12 or 1.00E+12: $1.0 \times 10^{12}$ (cells)

(i) DCs obtained by culturing precursor cells for 42 days under the condition of the FS36 administration group;

(ii) DCs obtained by culturing precursor cells for 21 days under the condition of the FS36 administration group, followed by seven days of culture under the medium condition of the GMIL-4 administration group; and (iii) DCs obtained by culturing precursor cells for seven days under the condition of the GMIL-4 administration group.

Figure 3:
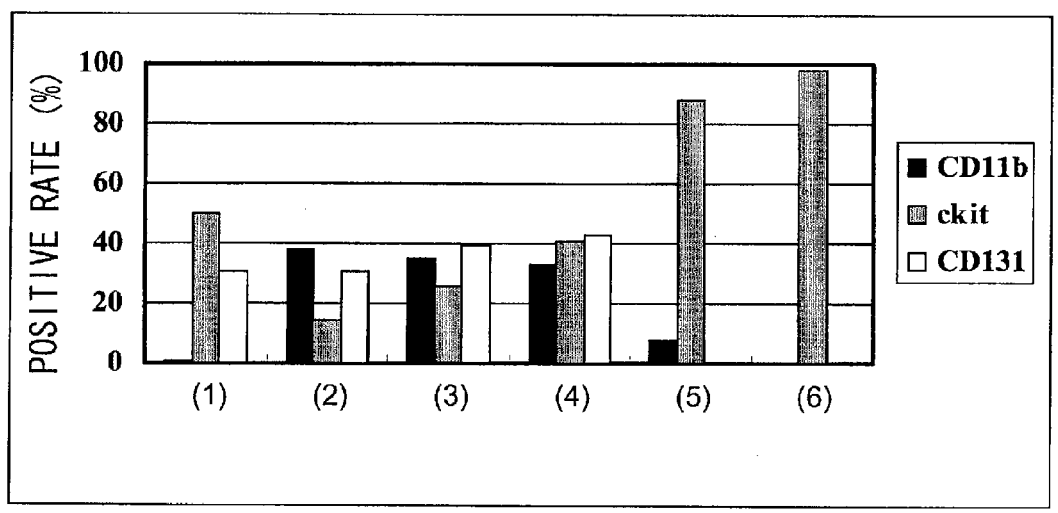

FIG. 3 shows the shifts in CD11b, c-kit, and CD131 positive rates for DC precursor cell growth during culture period. The left, middle, and right columns represent the proportion of CD11b$^+$ cells, c-kit$^+$ cells, or CD131 cells, respectively. Each of the samples (1) to (6) indicated in the figure are DCs produced under the following culture conditions:

(1): Normal DCs;
(2): One week of culture under the condition of the FS36 administration group, followed by one week of culture under the medium condition of the GMIL-4 administration group;

(3): Two weeks of culture under the condition of the FS36 administration group, followed by one week of culture under the medium condition of the GMIL-4 administration group;

(4): Three weeks of culture under the condition of the FS36 administration group, followed by one week of culture under the medium condition of the GMIL-4 administration group;

(5): Four weeks of culture under the condition of the FS36 administration group, followed by one week of culture under the medium condition of the GMIL-4 administration group; and (6): Five weeks of culture under the condition of the FS36 administration group, followed by one week of culture under the medium condition of the GMIL-4 administration group.

Figure 4:
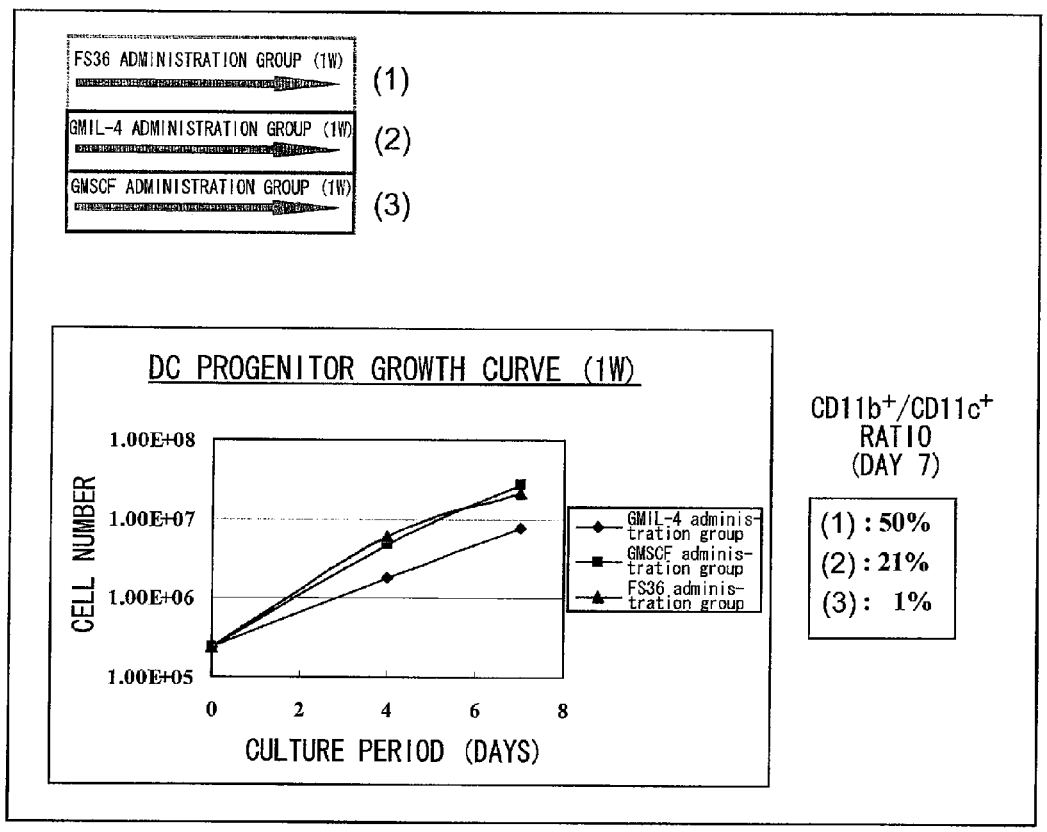

FIG. 4 shows the growth curve and CD11b$^+$/CD11c$^+$ ratio for DC precursor cells cultured for one week under the conditions of FS36 administration group (1), GMIL-4 administration group (2), and GMSCF administration group (3).

Figure 5:
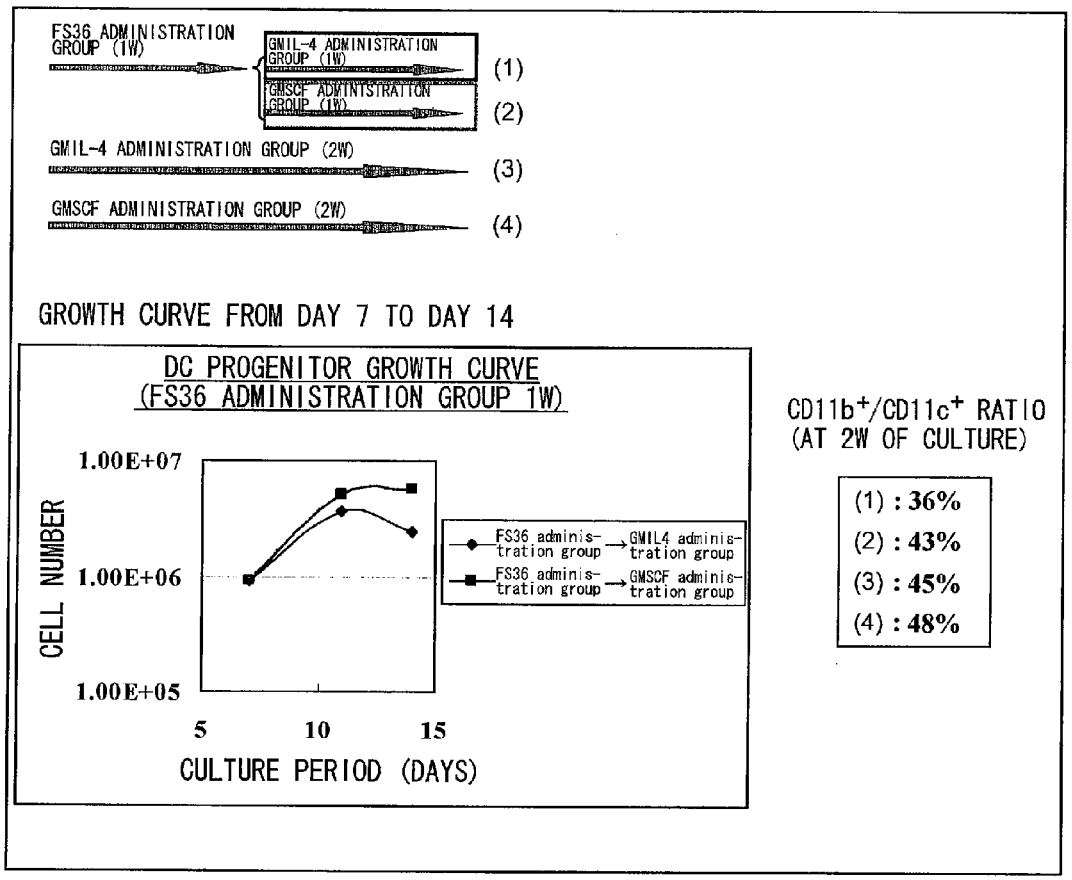

FIG. 5 shows the CD11b$^+$/CD11c$^+$ ratio and growth curve in samples (1) to (4) during culture period. (1) to (4) are DCs produced under the following culture conditions:

(1): One week of culture under the condition of the FS36 administration group, followed by one week of culture under the medium condition of the GMIL-4 administration group;

(2): One week of culture under the condition of the FS36 administration group, followed by one week of culture under the medium condition of the GMSCF administration group;

(3): Two weeks of culture under the condition of the GMIL-4 administration group; and (4): Two weeks of culture under the condition of the GMSCF administration group.

Figure 6:
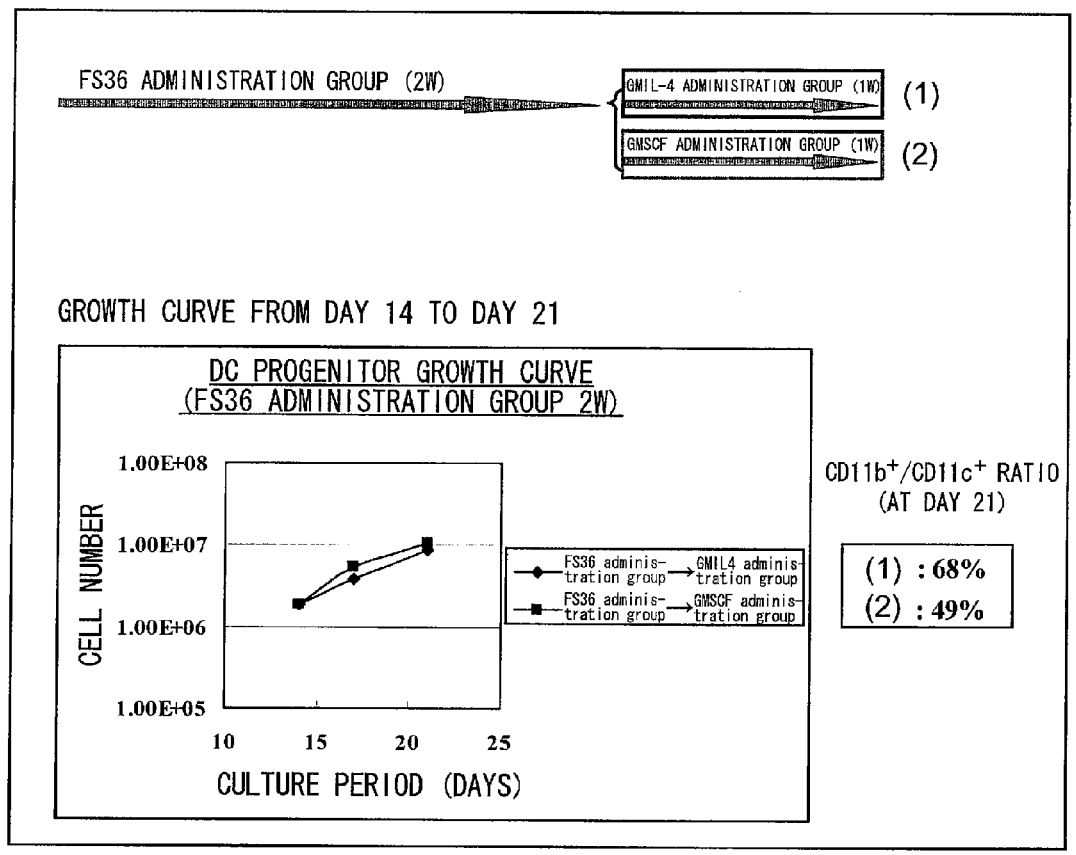

FIG. 6 shows the CD11b$^+$/CD11c$^+$ ratio and growth curve for samples (1) to (2) during culture period. (1) to (2) are DCs produced under the following culture conditions:

(1) Two weeks of culture under the condition of the FS36 administration group, followed by one week of culture under the medium condition of the GMIL-4 administration group; and (2) Two weeks of culture under the condition of the FS36 administration group, followed by one week of culture under the medium condition of the GMSCF administration group.

Figure 7:
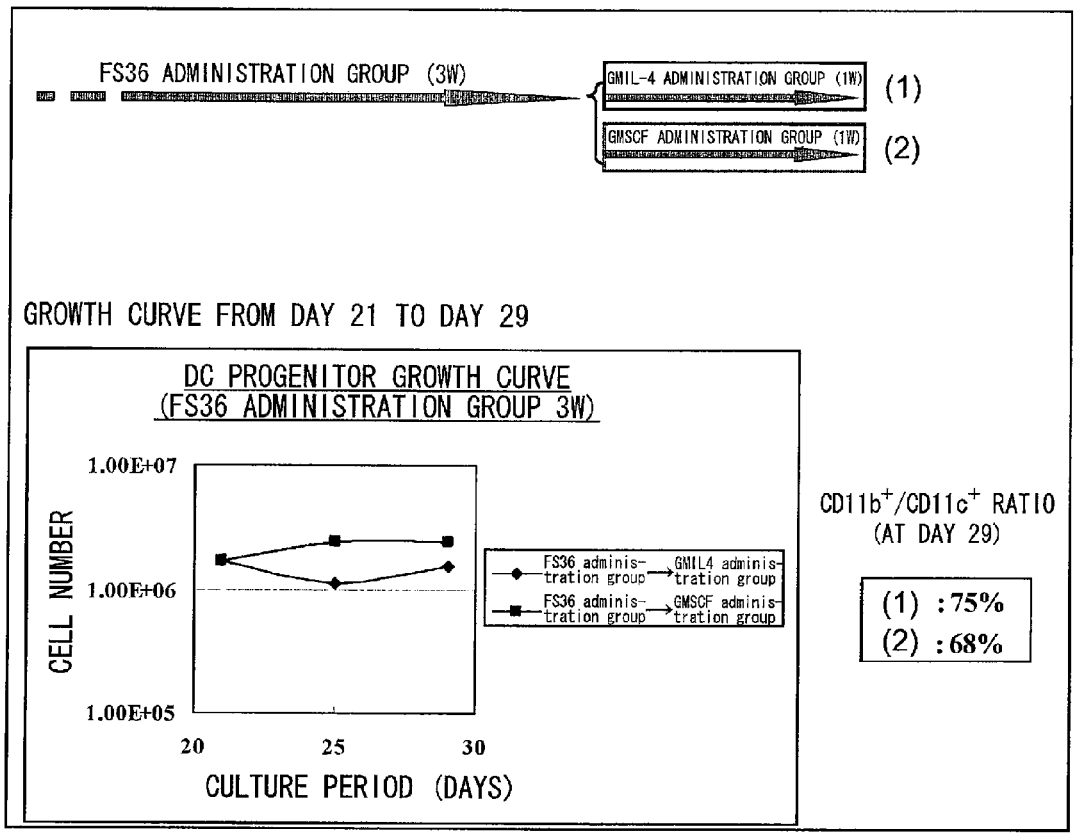

FIG. 7 shows the CD11b$^+$/CD11c$^+$ ratio and growth curve for samples (1) to (2) during culture period. (1) to (2) are DCs produced under the following culture conditions:

(1): Three weeks of culture under the condition of the FS36 administration group, followed by one week of culture under the medium condition of the GMIL-4 administration group; and (2): Three weeks of culture under the condition of the FS36 administration group, followed by one week of culture under the medium condition of the GMSCF administration group.

Figure 8:
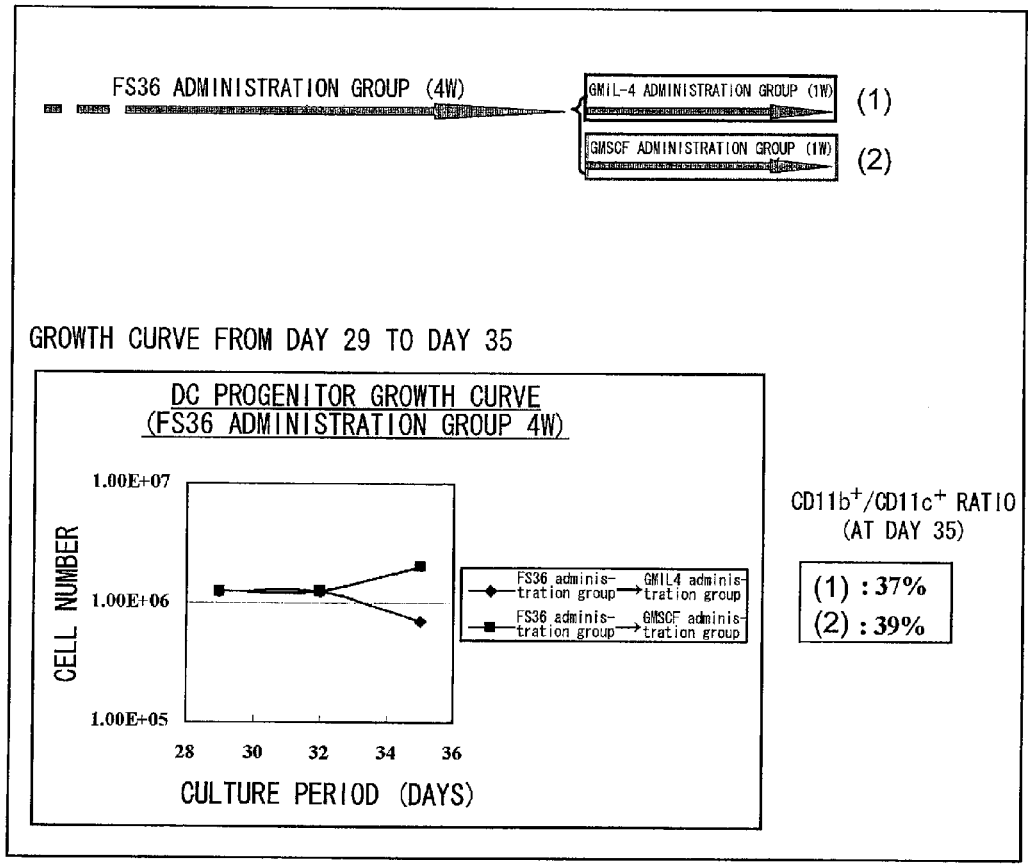

FIG. 8 shows the CD11b$^+$/CD11c$^+$ ratio and growth curve for samples (1) to (2) during culture period. (1) to (2) are DCs produced under the following culture conditions:

(1): Four weeks of culture under the condition of the FS36 administration group, followed by one week of culture under the medium condition of the GMIL-4 administration group; and (2): Four weeks of culture under the condition of the FS36 administration group, followed by one week of culture under the medium condition of the GMSCF administration group.

Figure 9:
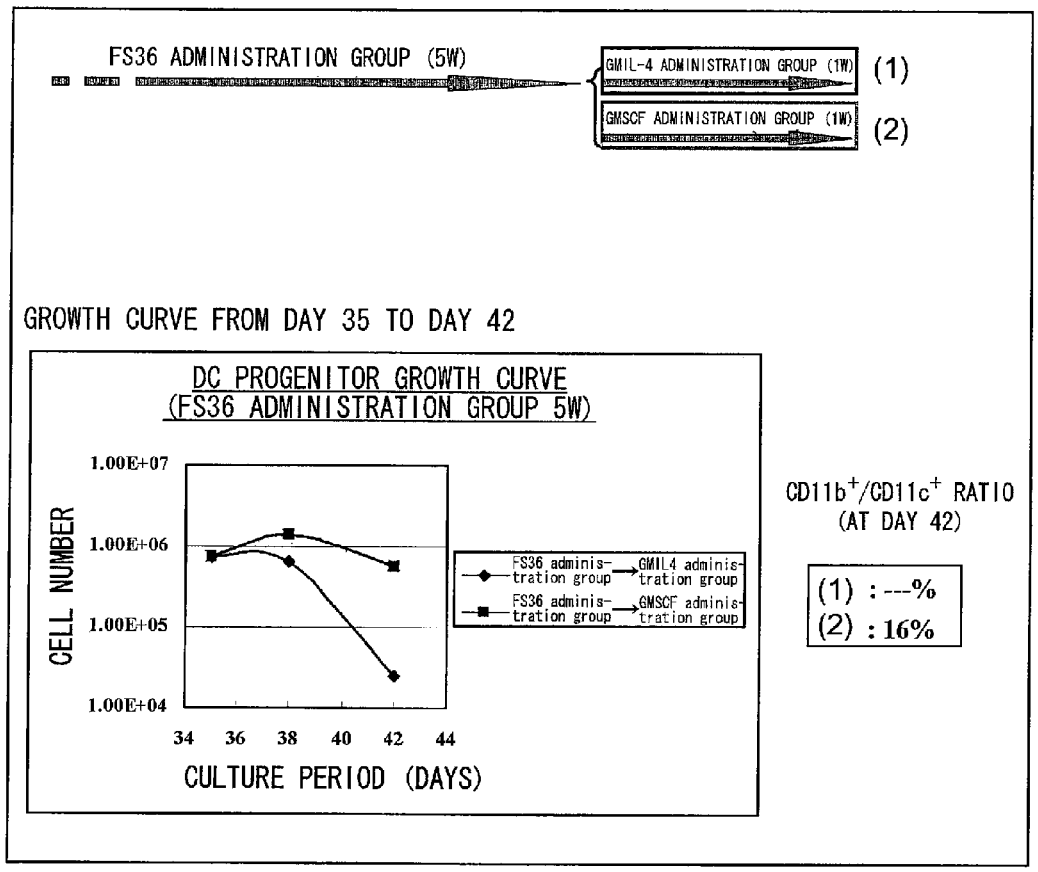

FIG. 9 shows the CD11b$^+$/CD11c$^+$ ratio and growth curve for samples (1) to (2) during culture period. (1) to (2) are DCs produced under the following culture conditions:

(1): Five weeks of culture under the condition of the FS36 administration group, followed by one week of culture under the medium condition of the GMIL-4 administration group; and (2): Five weeks of culture under the condition of the FS36 administration group, followed by one week of culture under the medium condition of the GMSCF administration group.

Figure 10:
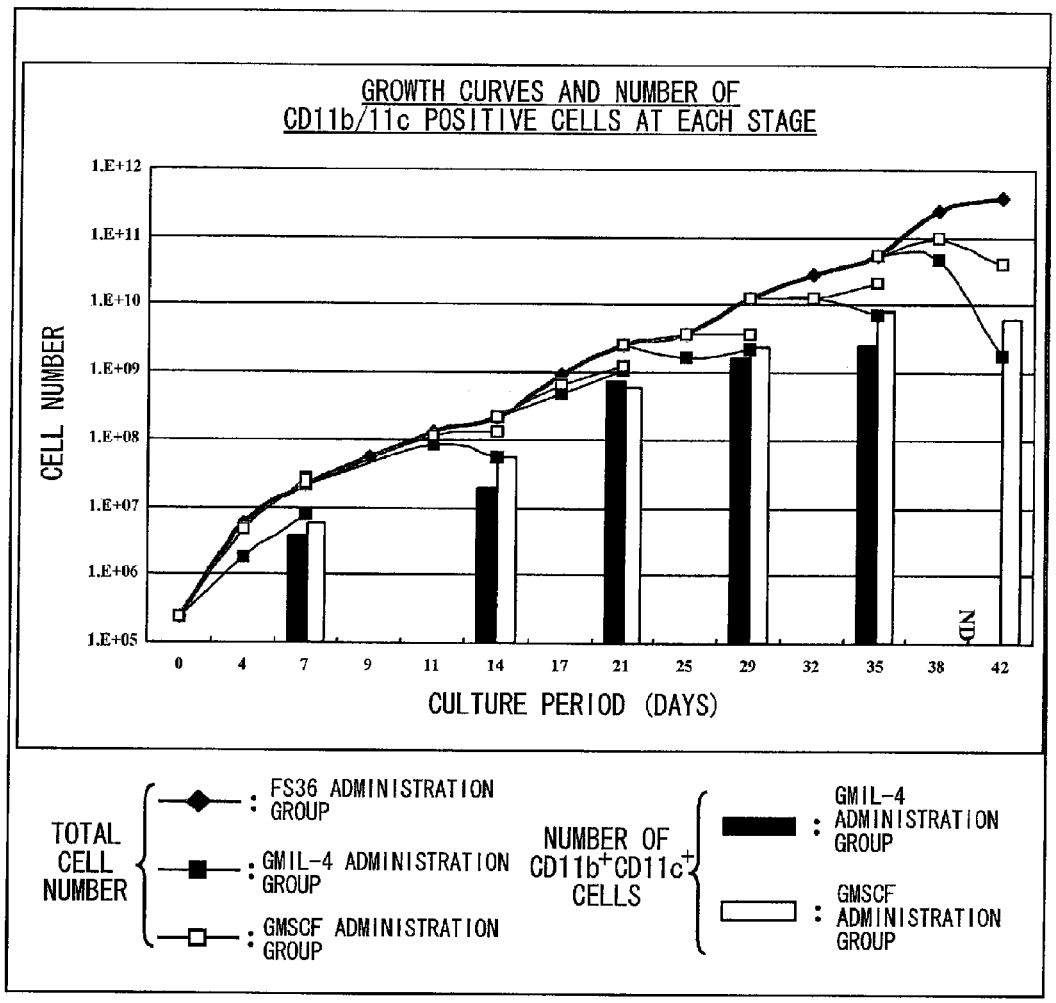

FIG. 10 shows shift in the cell number as well as the number of CD11b$^+$ CD11c$^+$ cells obtained during culture period for DC precursor cells cultured under the condition of the GMIL-4 administration group or GMSCF administration group, following culture under the condition of FS36 administration group.

Figure 11:
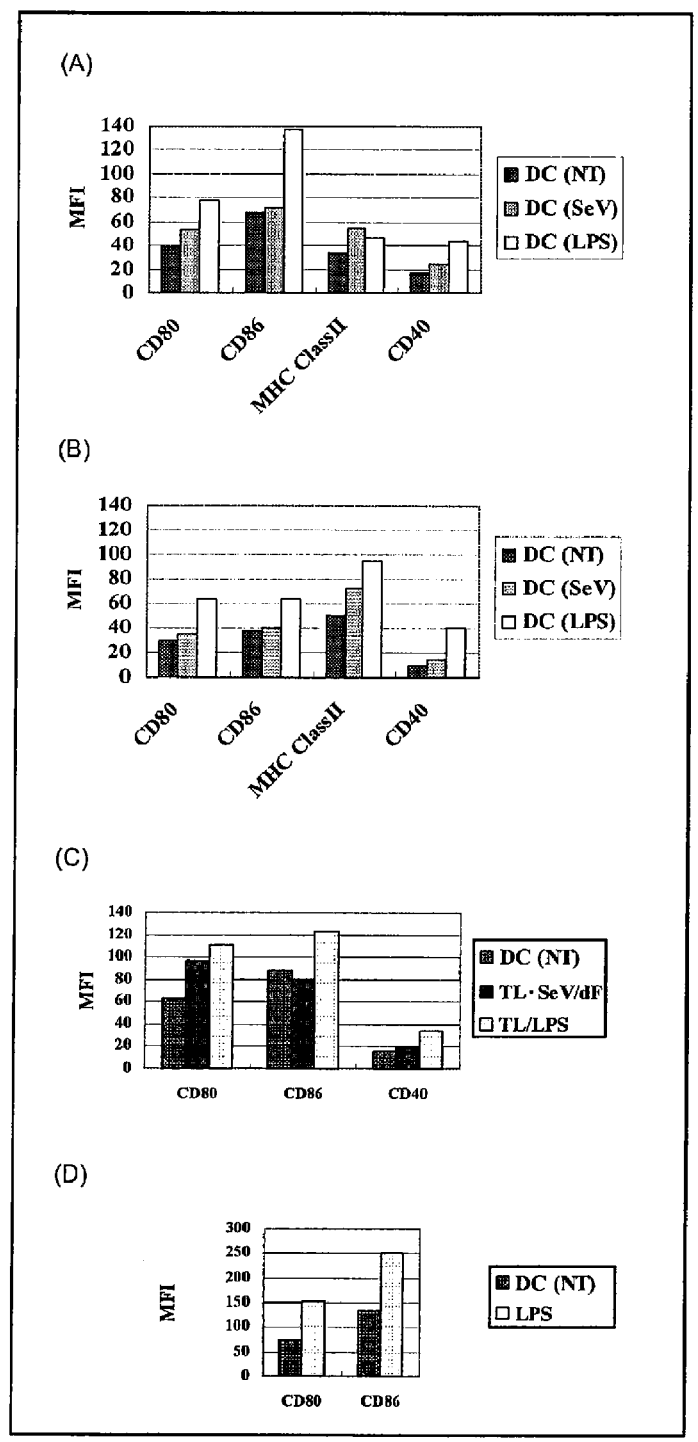

FIG. 11 shows a comparison of the expression levels of CD80, CD86, MHC class II, and CD40 two days after addition of F gene-deficient Sendai virus (SeV/dF) (abbreviated as DC(SeV) in this figure) or LPS (abbreviated as DC(LPS) in this figure) to the DCs of (A) to (D) described below. The result for the control (no addition) is also shown with the abbreviation DC(NT) in this figure. DCs of (A) to (D) in this figure are as follows:

(A): DCs obtained by three weeks of culture under the condition of the FS36 administration group, followed by one week of culture under the medium condition of the GMIL-4 administration group;

(B): Normal DCs;

(C): DCs obtained by two weeks of culture under the condition of the FS36 administration group, followed by one week of culture under the medium condition of the GMIL-4 administration group; and (D): DCs obtained by four weeks of culture under the condition of the FS36 administration group, followed by one week of culture under the medium condition of the GMIL-4 administration group.

Figure 12:
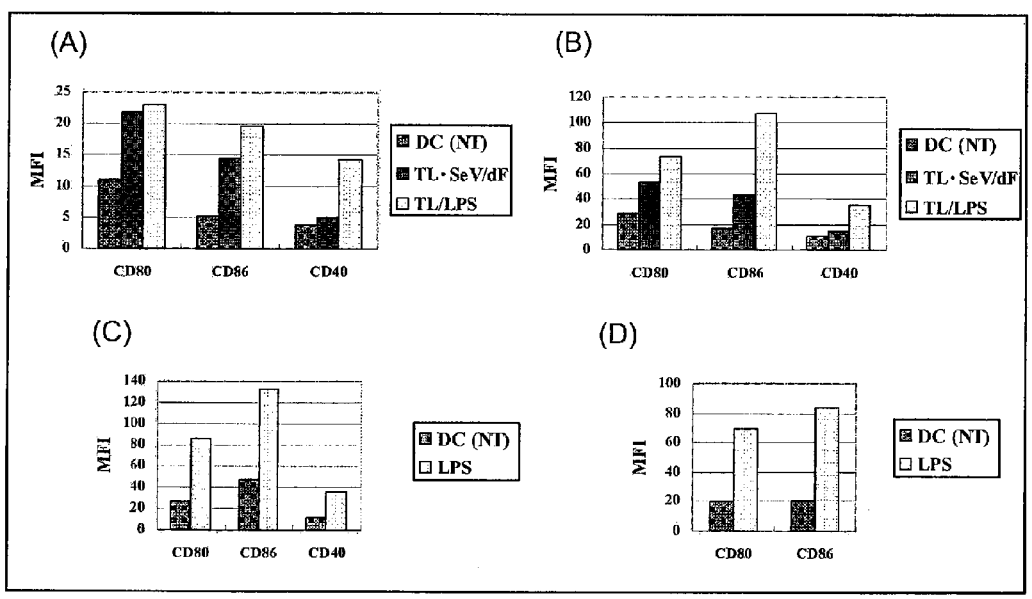

FIG. 12 shows a comparison of the expression levels of CD80, CD86, and CD40 two days after addition of F gene-deficient Sendai virus (SeV/dF) or LPS to the DCs of (A) to (D) described below. The result for the control (no addition) is also shown (DC(NT)). DCs of (A) to (D) in this figure are as follows:

(A): DCs obtained by one week of culture under the condition of the GMSCF administration group;

(B): DCs obtained by two weeks of culture under the condition of the FS36 administration group, followed by one week of culture under the medium condition of the GMSCF administration group;

(C): DCs obtained by three weeks of culture under the condition of the FS36 administration group, followed by one week of culture under the medium condition of the GMSCF administration group; and (D): DCs obtained by four weeks of culture under the condition of the FS36 administration group, followed by one week of culture under the medium condition of the GMSCF administration group.

Figure 13:
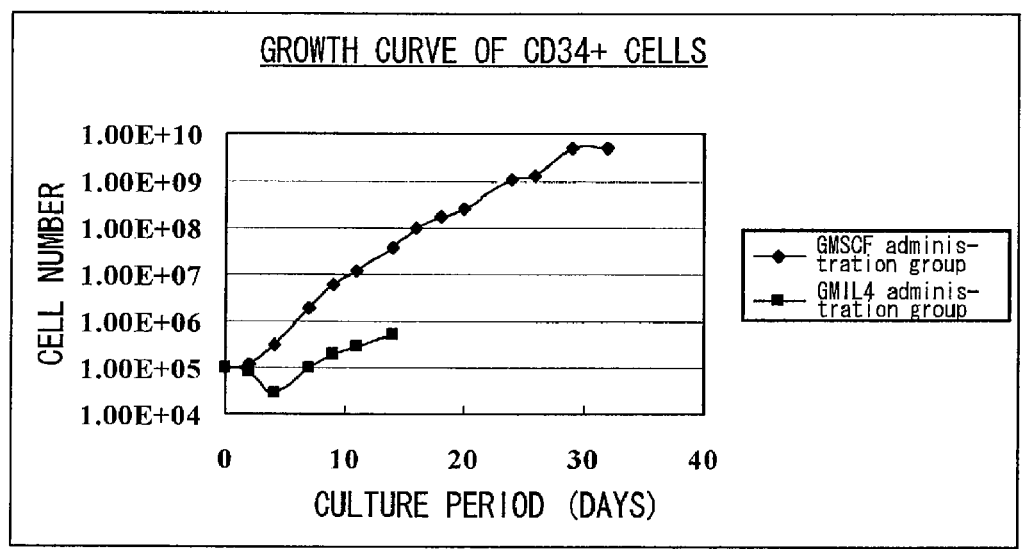

FIG. 13 is a growth curve of human CD34$^+$ cells, showing cell growth in the medium condition of the GMIL-4 administration group (1) or GMSCF administration group.

Figure 14:
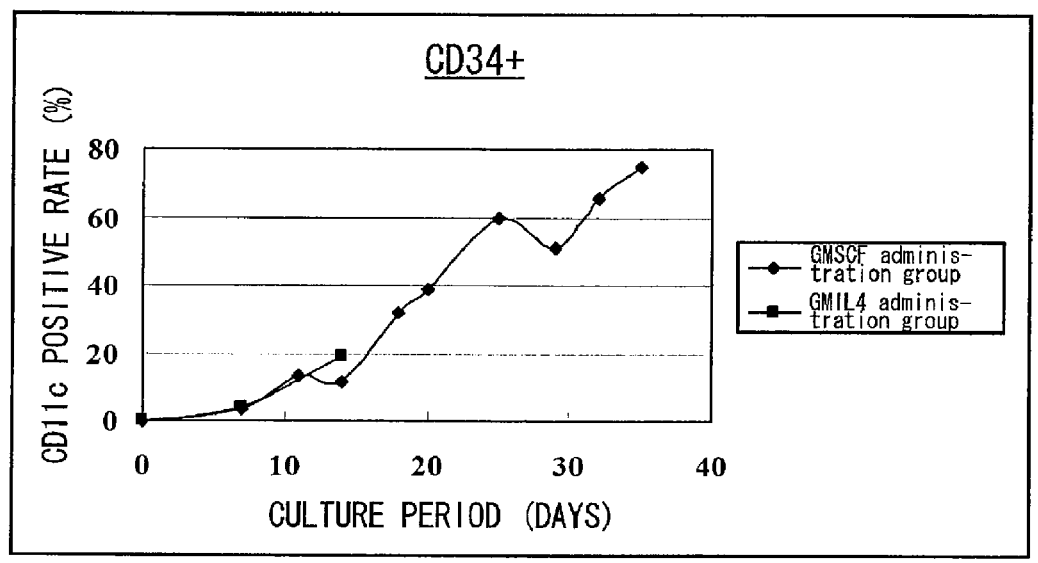

FIG. 14 shows shift in the CD11c$^+$ rate of human CD34$^+$ cells. The shift in the CD11c$^+$ rate was determined by culturing the cells in the medium condition of the GMIL-4 administration group (1) or GMSCF administration group.

Figure 15:
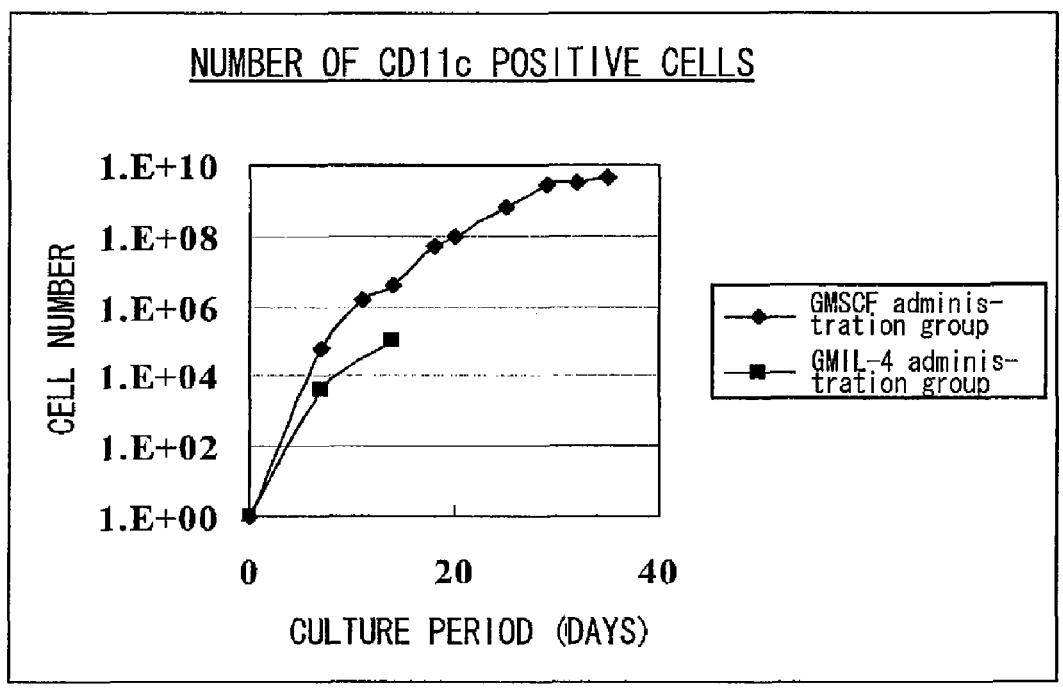

FIG. 15 shows shift in the number of CD11c$^+$ cells (total cell count×CD11c$^+$ percentage) obtained from human CD34$^+$ cells. The number of CD11c$^+$ cells was measured after cells were cultured in the medium condition of the GMIL-4 administration group (1) or GMSCF administration group.

Figure 16:
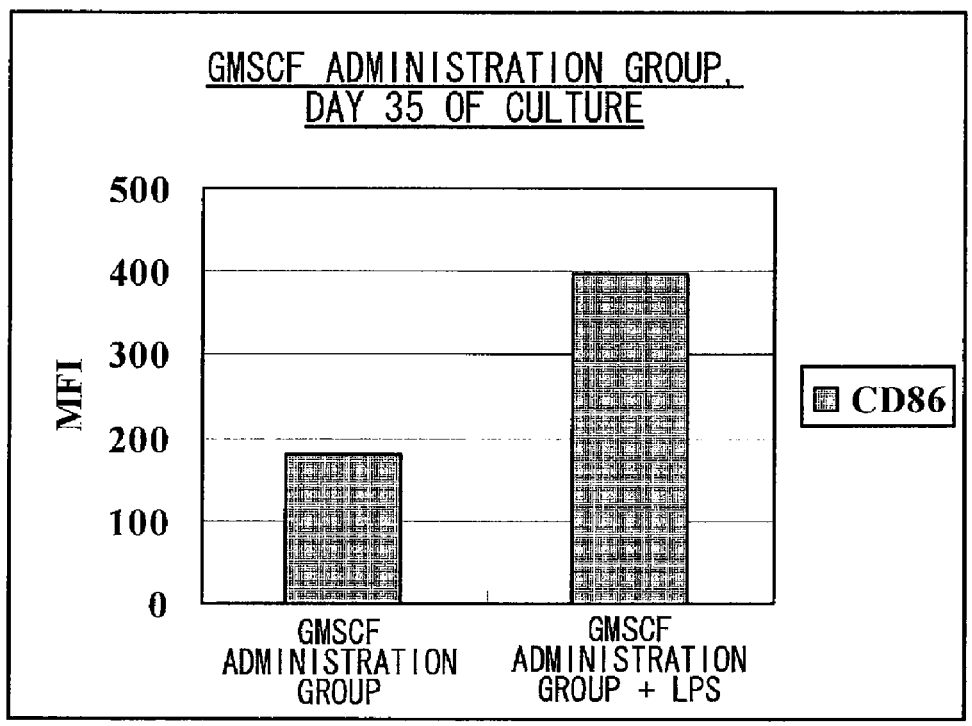

FIG. 16 shows a comparison of the expression level of CD86 in human CD34$^+$ cells cultured for 35 days under the condition of the GMSCF administration group and in human CD34$^+$ cells stimulated with LPS for the last three days of the 35 days. Human cord blood DC precursor cells differentiate simultaneously along with the amplification of GM-CSF and SCF.

Figure 17:
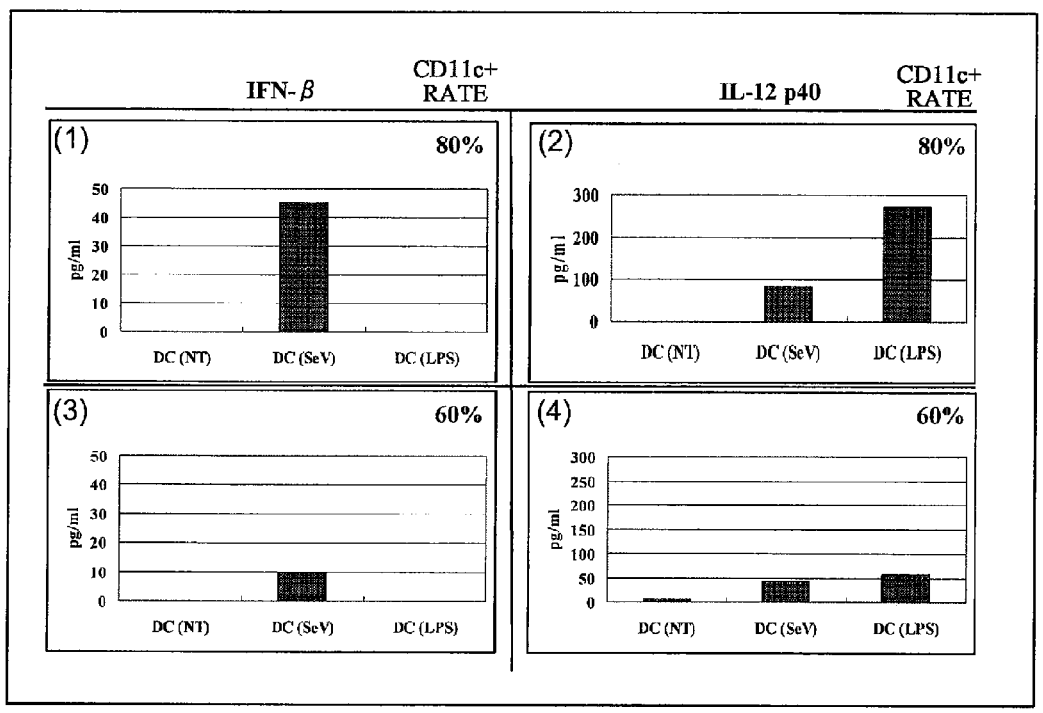

FIG. 17 shows result of the amount of cytokines produced by DCs cultured for three weeks under the condition of the FS36 administration group, then for one week under the medium condition of the GMIL-4 administration group, as assessed by ELISA. The amount of cytokines produced was measured using as samples the culture supernatants ($10^5$ cells/ml) two days after addition of F gene-deficient Sendai virus (SeV/dF) (abbreviated as SeV in this figure) or LPS (abbreviated as LPS in this figure) to the DCs. DC(NT) in this figure refers to a sample to which neither F gene-deficient Sendai virus (SeV/dF) nor LPS was added. Similarly to DCs not treated with cytokines, DCs cultured for one week under the condition of the GMIL-4 administration group were confirmed to produce IL-12 and IFN-β. Details of (1) to (4) in this figure are as follows:

(1): measurement results of the amount of IFN-β produced in DCs obtained after three weeks of culture under the condition of the FS36 administration group, followed by one week of culture under the medium condition of the GMIL-4 administration group;

(2): measurement results of the amount of IL-12 produced in DCs obtained after three weeks of culture under the condition of the FS36 administration group, followed by one week of culture under the medium condition of the GMIL-4 administration group;

(3): measurement results of the amount of IFN-β produced in normal DCs; and (4): measurement results of the amount of IL-12 produced in normal DCs.

Figure 18:
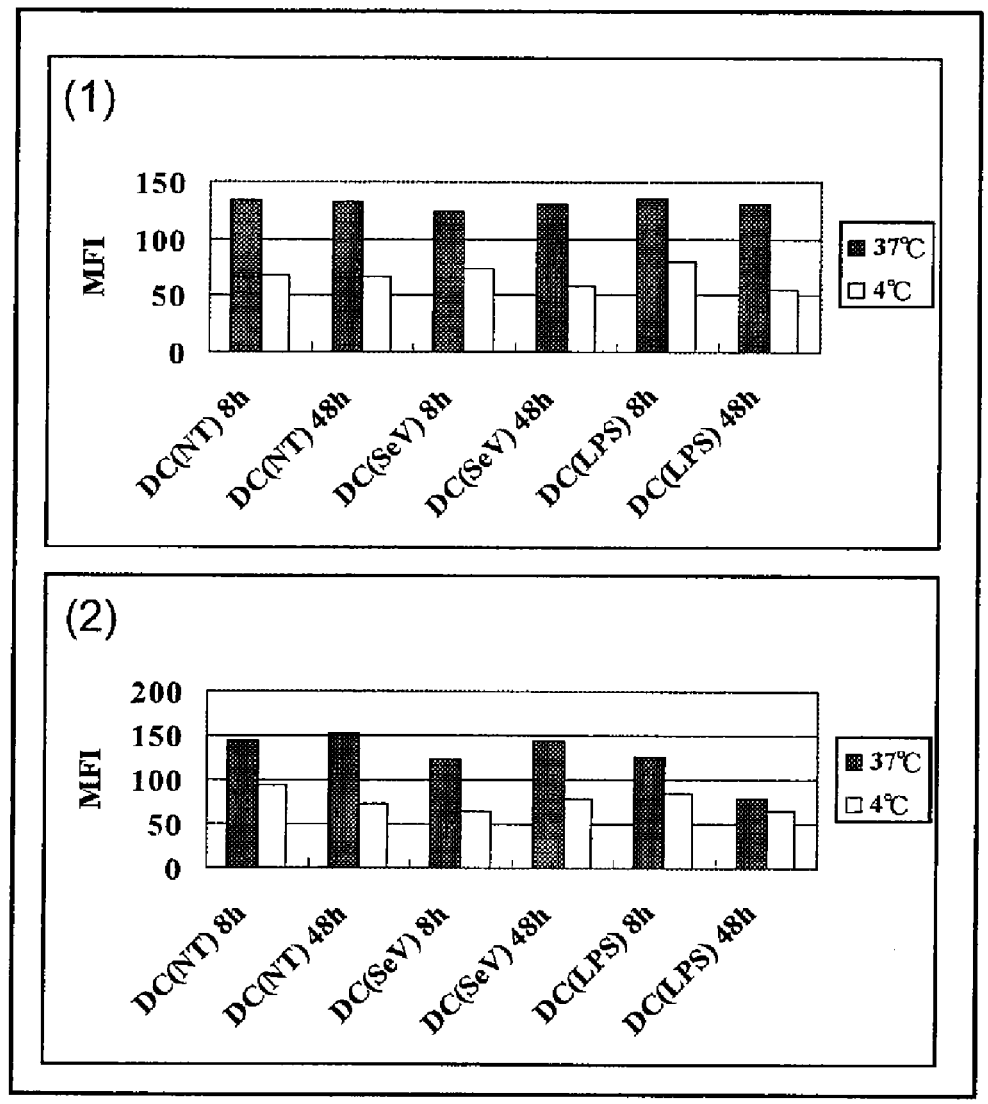

FIG. 18 The ability to uptake FITC-dextran (endo-/phagocytotic activity) was assessed two days after addition of F gene-deficient Sendai virus (SeV/dF) or LPS to DCs obtained by culturing under the condition of the FS36 administration group, followed by one week of culture under the medium condition of the GMSCF administration group. DC(NT) in this figure refers to samples to which neither F gene-deficient Sendai virus (SeV/dF) (indicated as SeV is the figure) nor LPS (indicated as LPS in the figure) was added. Dendritic cells actively uptake FITC-dextran (MW=40,000) at 37° C.; however, the uptake is inhibited at 4° C. Incorporation of FITC-dextran (1 mg/ml) was carried out at 37° C. and 4° C. for 30 minutes in each reaction. DCs obtained by culture under the condition of the FS36 administration group, followed by one week of culture under the medium condition of the GMSCF administration group retained the ability to incorporate antigens. Details of (1) and (2) in this figure are as follows:

(1): measurement results of DCs obtained by three weeks of culture under the condition of the FS36 administration group, followed by one week of culture under the medium condition of the GMIL-4 administration group; and (2): measurement results of normal DCs.

Figure 19:
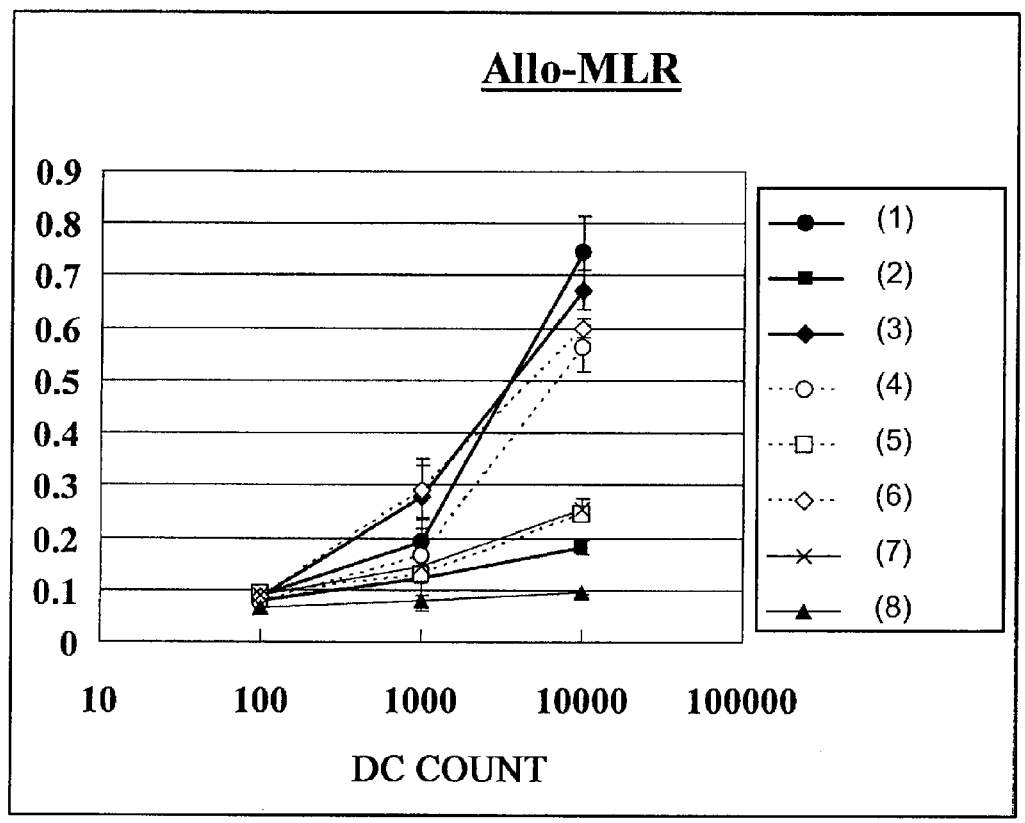

FIG. 19. The intensity of stimulation towards T cell (C57BL/6) growth by DCs obtained by culture under the condition of the FS36 administration group, followed by one week of culture under the medium condition of the GMSCF administration group was measured. $10^6$ T cells were used for each case. DCs obtained by culture under the condition of the FS36 administration group, followed by one week of culture under the medium condition of the GMSCF administration group retained the ability to proliferate/activate T cells.

(1): Measurement results for DCs obtained by three weeks of culture under the condition of the FS36 administration group, followed by one week of culture under the medium condition of the GMIL-4 administration group (sample without stimulation by F gene-deficient Sendai virus (SeV/dF) or LPS).

(2): Measurement results for a sample two days after addition of F gene-deficient Sendai virus (SeV/dF) to DCs obtained by three weeks of culture under the condition of the FS36 administration group, followed by one week of culture under the medium condition of the GMIL-4 administration group.

(3): Measurement results for a sample two days after addition of LPS to DC precursor cells obtained by three weeks of culture under the condition of the FS36 administration group, followed by one week of culture under the medium condition of the GMIL-4 administration group.

(4): Measurement results for normal DCs (DCs without stimulation by F gene-deficient Sendai virus (SeV/dF) or LPS).

(5): Measurement results for a sample two days after addition of F gene-deficient Sendai virus (SeV/dF) to normal DCs.

(6): Measurement results for a sample two days after addition of LPS to normal DCs.

(7): Measurement results for a sample of mixed culture of syngeneic lymphocytes.

(8): Measurement results for normal DCs themselves (without T cells).

Figure 20:
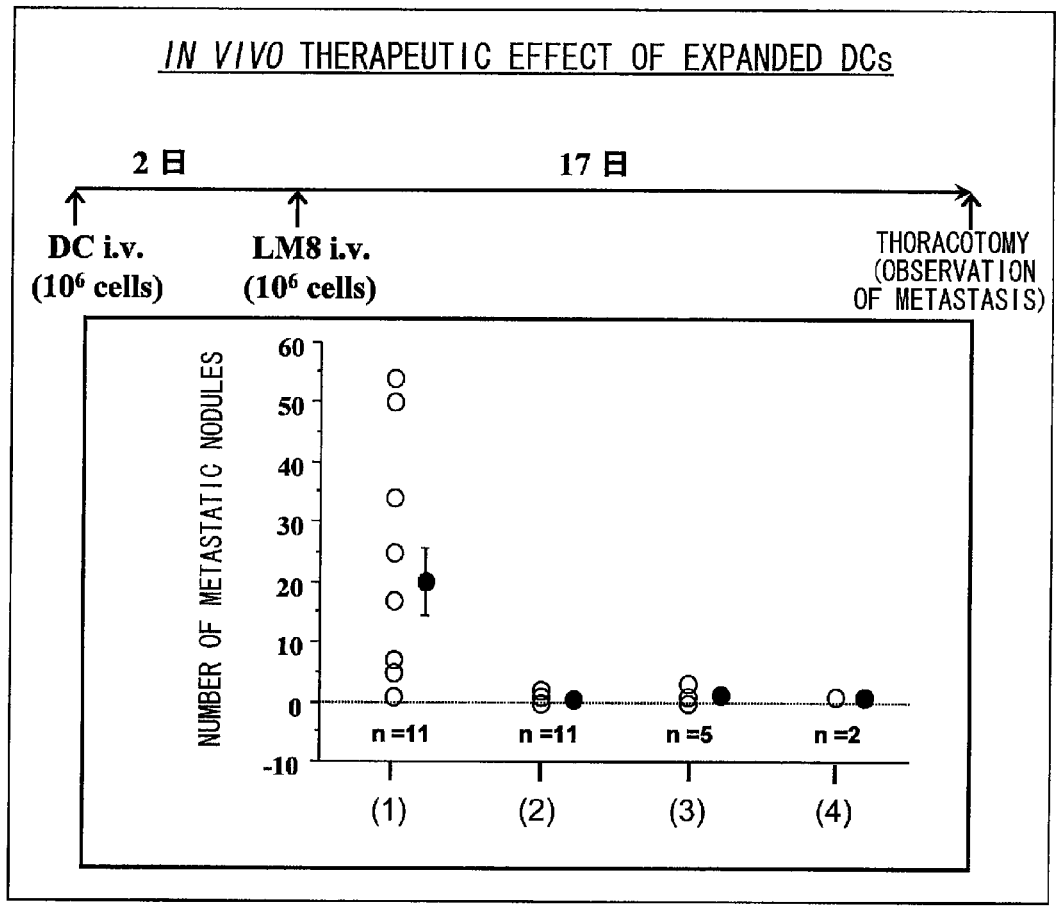

FIG. 20: DCs were prepared by culture under the condition of the FS36 administration group, followed by one week of culture under the medium condition of the GMSCF administration group, and were assessed for their in vivo therapeutic effect. Details of samples (1) to (4) in this figure are as follows:

(1): Results of counts of metastatic nodules in the lung of mice not administered with DCs.

(2): Results of counts of metastatic nodules in the lung of mice administered with normal DCs at the caudal vein.

(3): Results of counts of metastatic nodules in the lung of mice administered at the caudal vein, with DCs obtained by two weeks of culture under the condition of the FS36 administration group, followed by one week of culture under the medium condition of the GMIL-4 administration group.

(4): Results of counts of metastatic nodules in the lung of mice administered at the caudal vein with DCs obtained by three weeks of culture under the condition of the FS36 administration group, followed by one week of culture under the medium condition of the GMSCF administration group.

Figure 21:
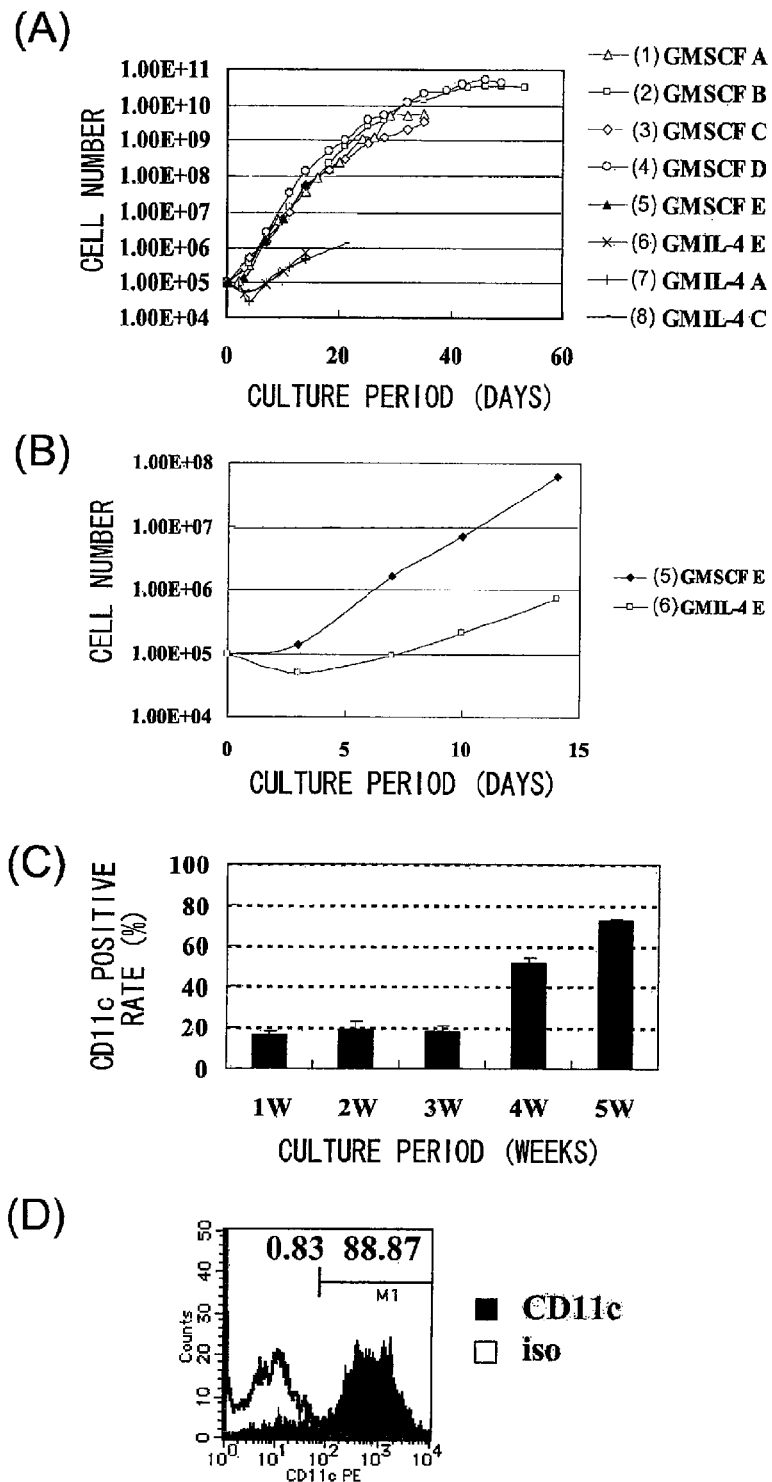

FIG. 21 shows the growth and differentiation curves of human cord blood-derived CD34$^+$ cells ((A) and (B)), and the proportion of CD11c-positive cells in the expanded cells (C). Fig. (B) shows details on the growth of the above-described cells for the administration groups of samples (5) and (6) of Fig. (A) during the culture period from day 0 to day 15. Furthermore, Fig. (D) shows results of FACS analysis obtained in a separate experiment for human cord blood-derived CD34$^+$ cells cultured in GMSCF medium for five weeks (CD11c positive rate=88.87%). In Fig. (D), the graph in black represents result for the CD11c antibody, while the graph in white represents result for an isotype control (iso). In Fig. (D), the values indicated at the right and left represent the number of cells (as percentage %) in the M1 area obtained with the CD11c antibody and isotype control (iso), respectively. Details of samples (1) to (8) in Fig. (A) are described below. The terminal letters A to E in the titles of samples (1) to (8) described in Figs. (A) and (B) indicate that they are results for cells derived from different subjects.

(1) to (5): Culture under the condition of the GMSCF administration group.

(6): Culture under the condition of the GMIL4 administration group.

(7) and (8): Culture under the condition of the GMIL4 administration group (1).

Figure 22:
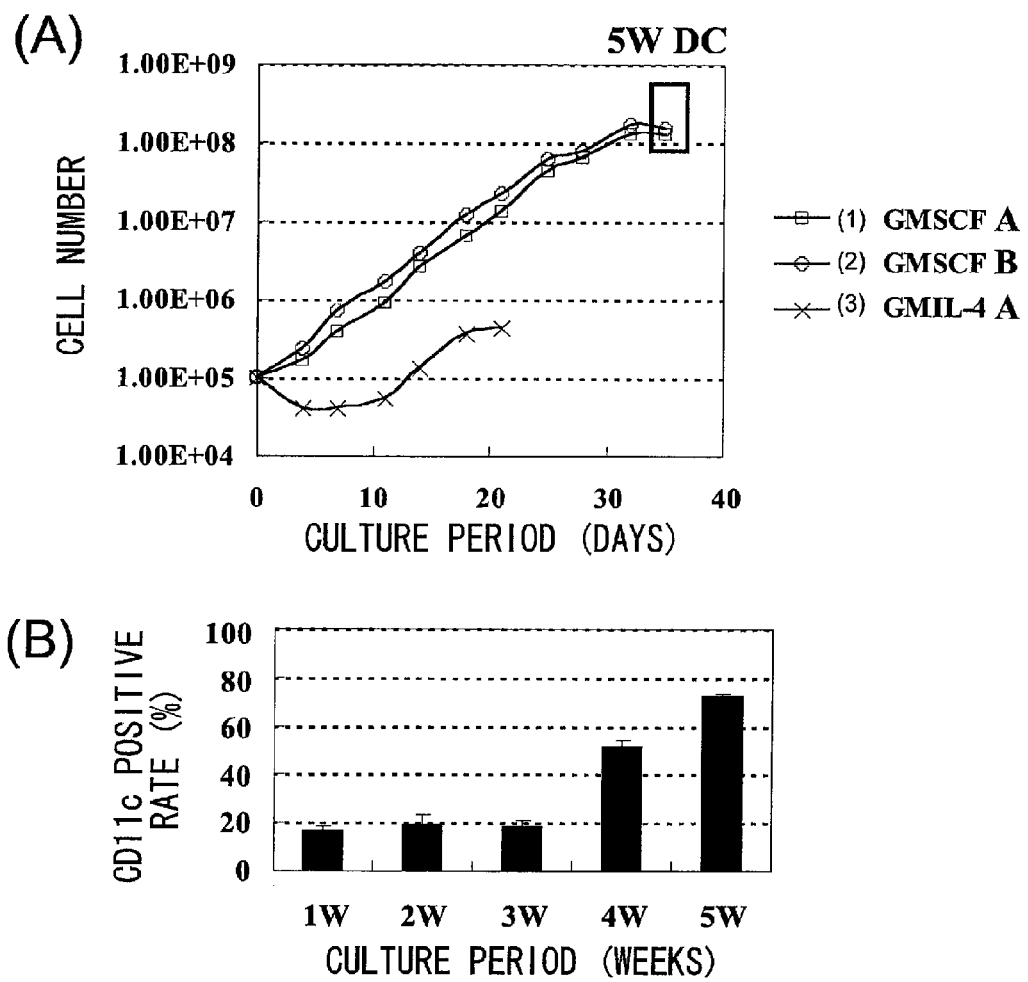

FIG. 22 shows a growth curve of human G-CSF-treated peripheral blood-derived CD34$^+$ cells (A), and the percentage of CD11c positive cells in the expanded cells (B). Details of samples (1) to (3) in this figure are described below. The terminal letters A and B in the titles of samples (1) to (3) described in FIG. (A) indicate that they are results for cells derived from different subjects.

(1) and (2): Culture under the condition of the GMSCF administration group.

(3): Culture under the condition of the GMIL4 administration group (1).

Figure 23:
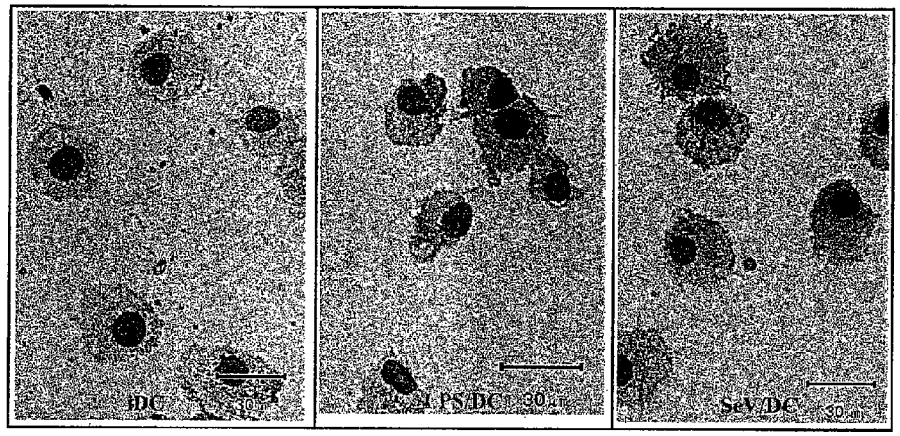
Figure 23:
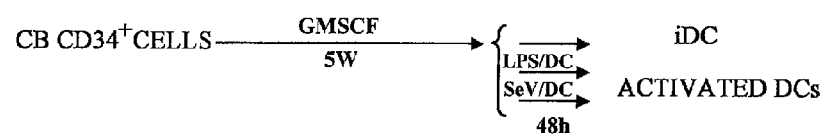
Figure 23:
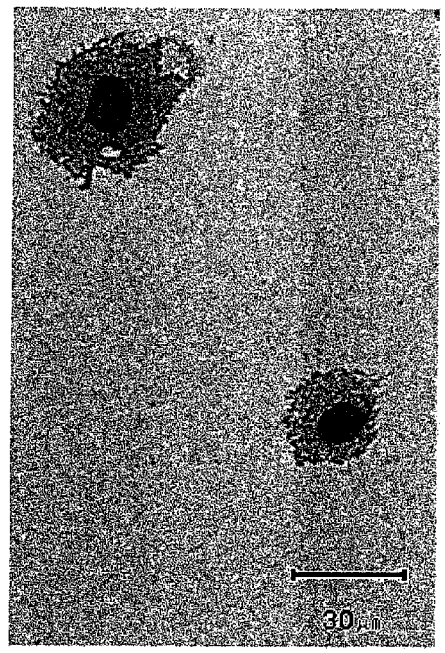

FIG. 23 shows results of assessment for the presence of dendrites in cells at day 35 of culture under the condition of the GMSCF administration group during the culture period of human cord blood-derived CD34$^+$ cells. Panel B is an enlargement of the sample in the middle of Panel A (sample cultured for five weeks under the condition of the GMSCF administration group, then stimulated with LPS for 48 hours). Dendrites can be clearly observed.

Figure 24:
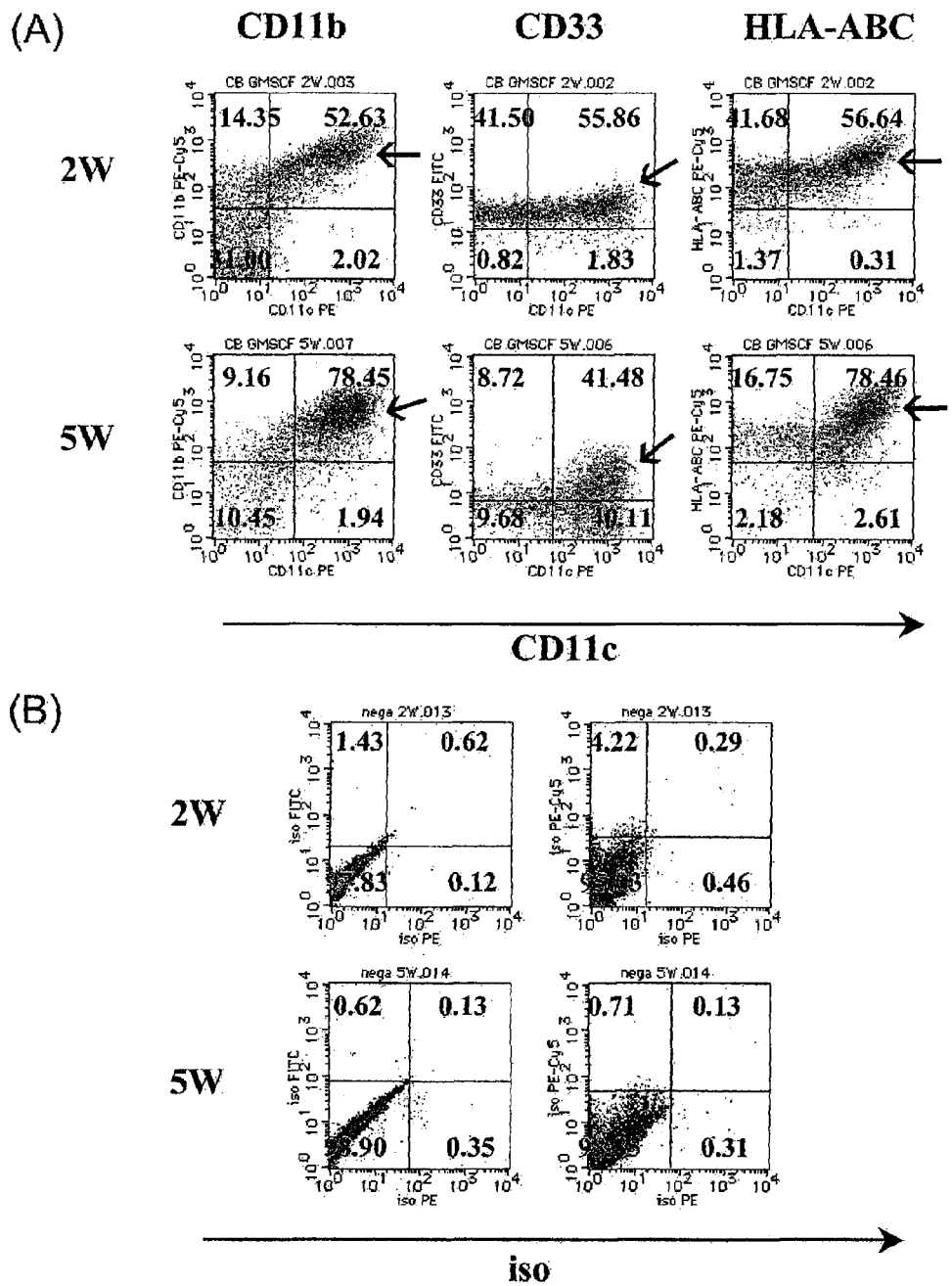

FIG. 24 shows results of the expression analysis for CD11b, CD33, and HLA-ABC in cells at day 14 (2 W) and day 35 (5 W) of culture (cells cultured under the condition of the GMSCF administration group) during the culture period of human cord blood-derived CD34$^+$ cells.

Figure 25:
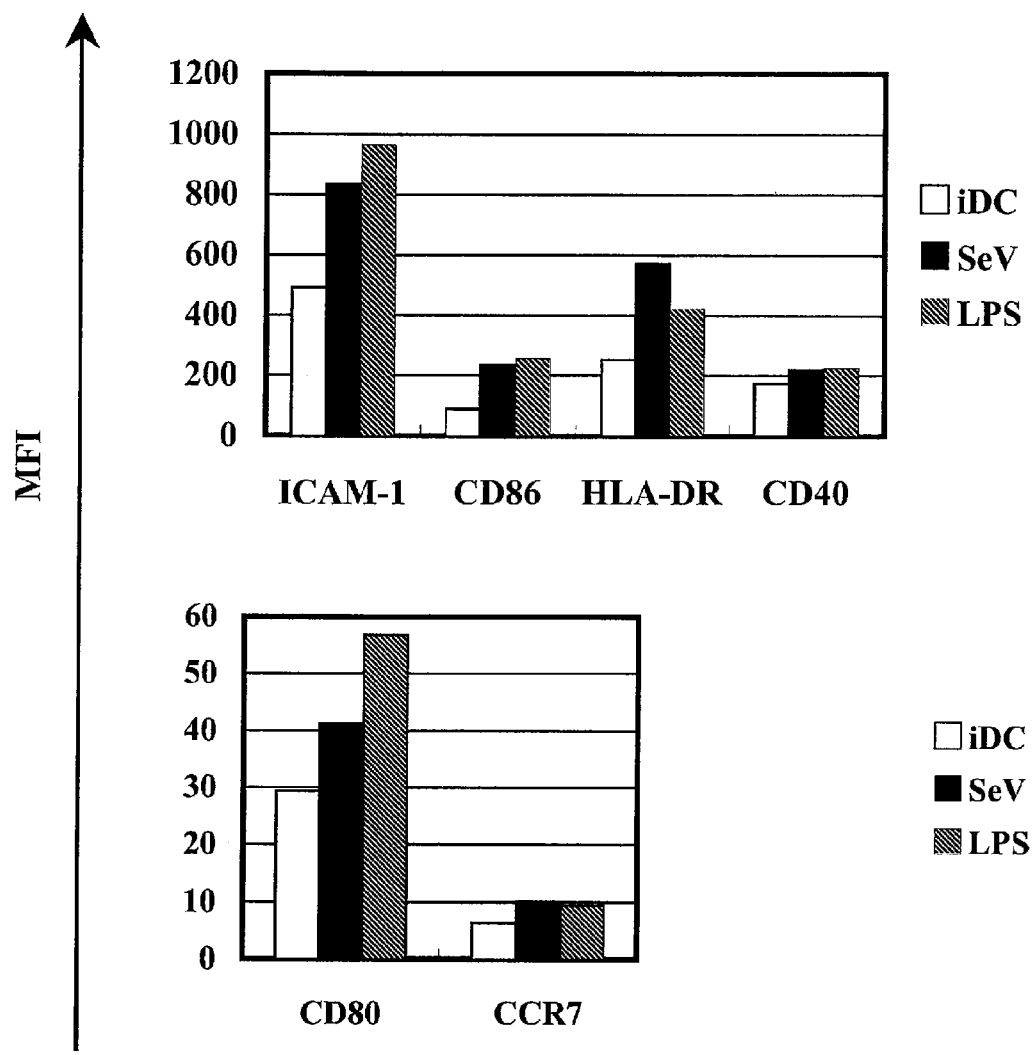

FIG. 25 shows results of the expression analysis for ICAM-1, CD86, HLA-DR, CD40, CD80, and CCR7 in cells at day 35 of culture during the culture period of human cord blood-derived CD34$^+$ cells under the treatment of LPS or SeV/dF. The abbreviations in this figure are as follows: iDC-iDC treatment; SeV-SeV/dF treatment; LPS-LPS treatment.

Figure 26:
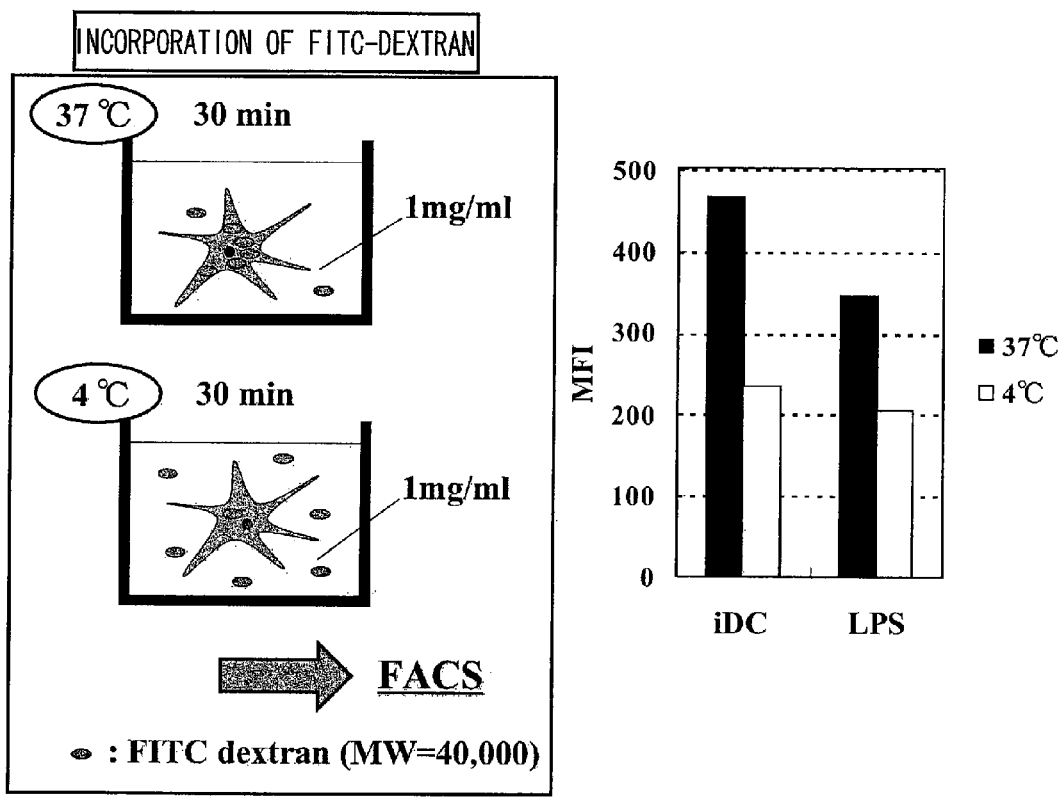

FIG. 26. The ability to incorporate FITC-dextran (endo-/phagocytotic activity) was assessed for immature DC (iDC) or DCs two days after addition of LPS using cells at day 35 of culture (cells cultured under the condition of the GMSCF administration group) during the culture period of human cord blood-derived CD34$^+$ cells. Dendritic cells actively uptake FITC-dextran (MW=40,000) at 37° C.; however, the uptake is inhibited at 4° C. Incorporation of FITC-dextran (1 mg/ml) was carried out at 37° C. and 4° C. for 30 minutes in each reaction. The result showed that like dendritic cells, the cells described above actively took up FITC-dextran (MW=40,000) at 37° C.; however, the uptake was inhibited at 4° C.

Figure 27:
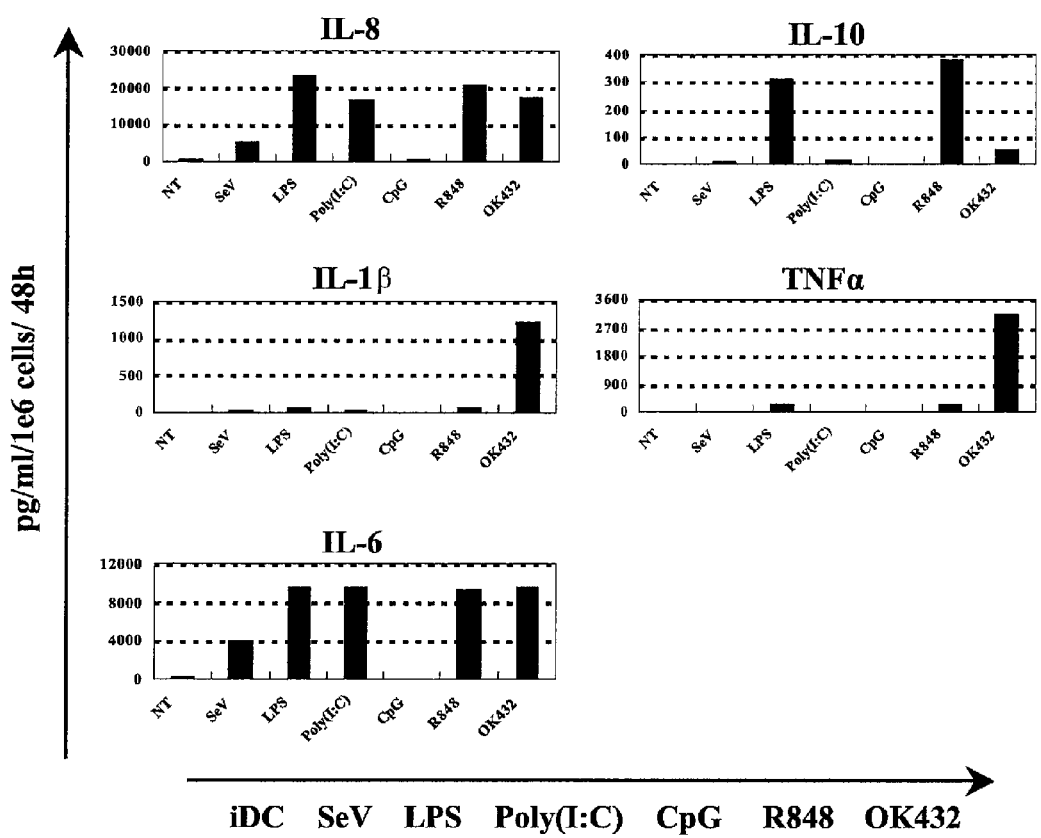

FIG. 27 shows results of ELISA assessment for the amount of cytokine produced in cells at day 35 of culture (cells cultured under the condition of the GMSCF administration group) during the culture period of human cord blood-derived CD34$^+$ cells. The cells cultured as described above were processed by the specified treatment below. Culture supernatants ($10^5$ cells/ml) after the above-described treatment were used as the sample for measuring the amount of cytokine produced. NT in this figure refers to a sample that did not undergo the specified treatment below. The "specified treatment" specifically refers to the following:

(1) iDC treatment: indicated as iDC in the figure.
(2) SeV/dF treatment: indicated as SeV in the figure.
(3) LPS treatment: indicated as LPS in the figure.
(4) Poly(I:C) treatment: indicated as Poly(I:C) in the figure.
(5) CpG treatment: indicated as CpG in the figure.
(6) R-848 treatment: indicated as R-848 in the figure.
(7) OK432 treatment: indicated as OK43 in the figure.

Figure 28:
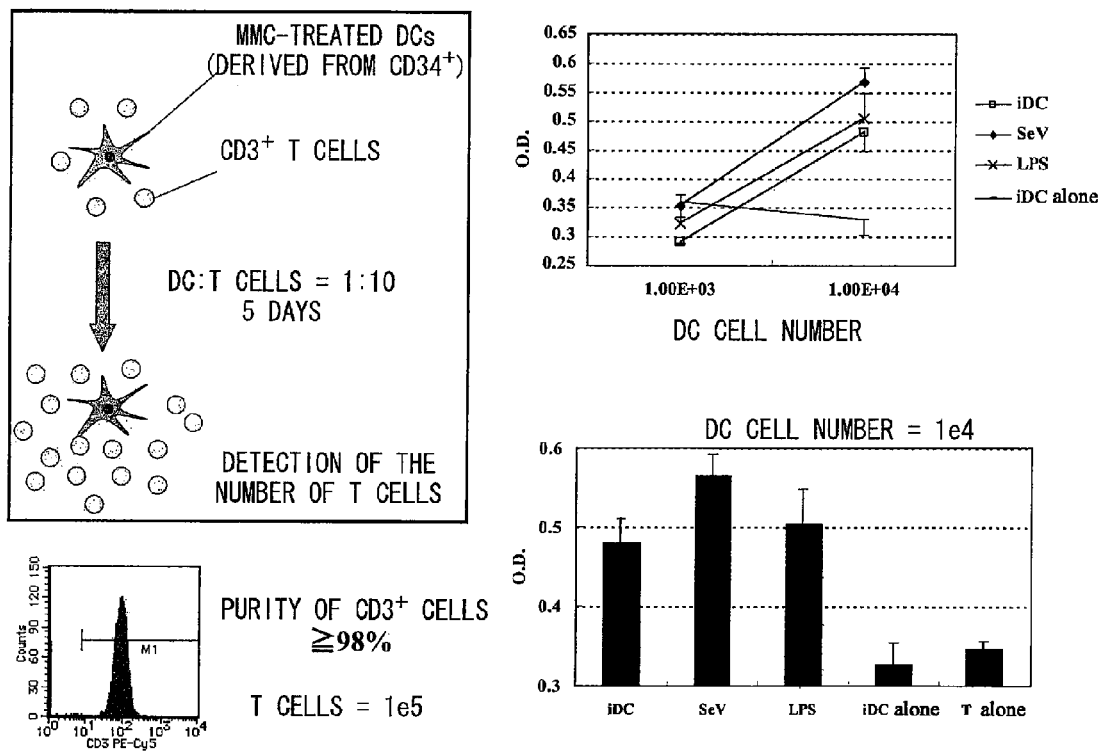

FIG. 28. The intensity of stimulation towards T cell growth (allogenic T cells from volunteers) was measured in cells at day 35 of culture (cells cultured under the conditions of (1) or (2) described in FIG. 21) during the culture period of human cord blood-derived CD34$^+$ cells. $10^5$ T cells were used for each case. In the upper right panel, the results obtained with a DC cell count of 1.00E+03 ($1 \times 10^3$ cells) correspond to the case where DC:CD3$^+$ T cells=1:100 (Mixture group 1), while the results obtained with a DC cell count of 1.00E+04 ($1 \times 10^4$ cells) correspond to the case where DC:CD3$^+$ T cells=1:10 (Mixture group 2). iDC: iDC+T cells; SeV: SeV-stimulated DCs+T cells; LPS: LPS-stimulated DCs+T cells; iDC alone: iDCs alone without T cells; T alone: T cells alone.

Figure 29:
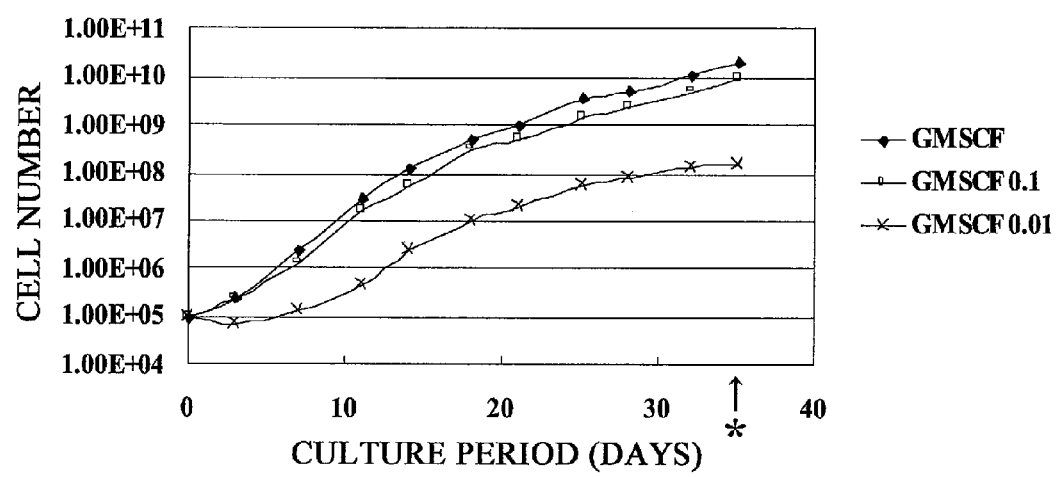

FIG. 29 shows results of human cord blood-derived CD34$^+$ cells under the conditions of (1) to (3) described below.

(1): the condition of the GMSCF administration group (indicated as "GMSCF" in this figure).

(2): the condition of the 0.1 GMSCF administration group (indicated as "GMSCF0.1" in this figure).

(3): the condition of the 0.01 GMSCF administration group (indicated as "GMSCF0.01" in this figure).

Figure 30:
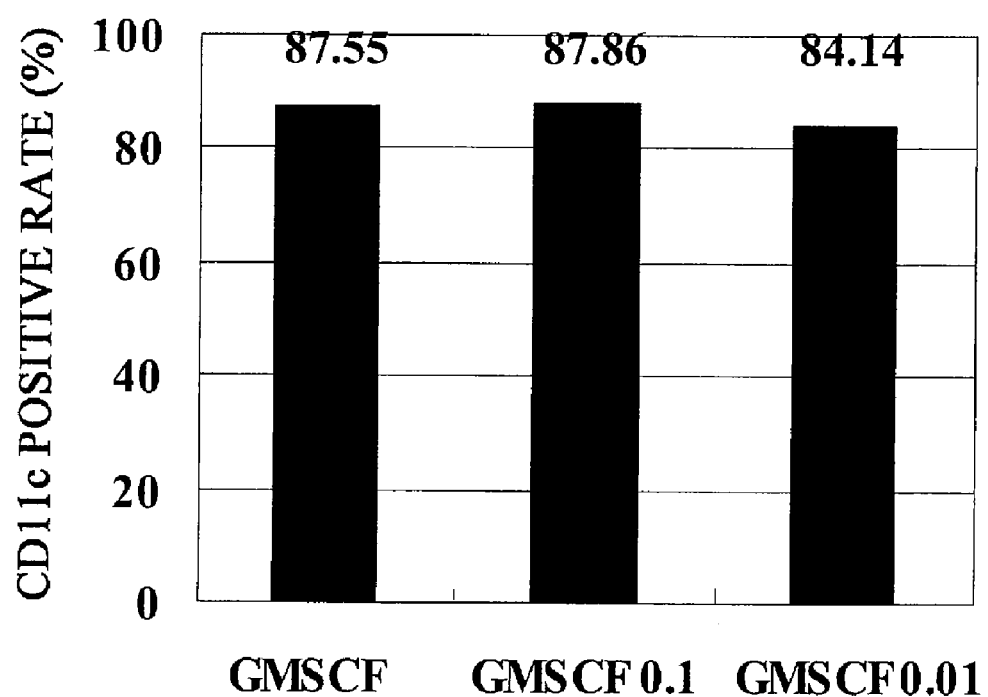

FIG. 30 shows measurement results (percentage) for CD11c-positive cells in the cells cultured under each of the conditions at the time point indicated with the asterisk (*) in FIG. 29 described above (i.e., at day 35 of culture). The abbreviations in this figure are as follows:

(1) GMSCF: Culture under the condition of the GMSCF administration group.

(2) GMSCF0.1: Culture under the condition of the 0.1 GMSCF administration group.

(3) GMSCF0.01: Culture under the condition of the 0.01 GMSCF administration group.

BEST MODE FOR CARRYING OUT THE INVENTION

The present invention relates to methods for producing dendritic cells, which comprise the step of culturing dendritic cell precursor cells in the presence of multiple cytokines. The step described above enables efficient expansion and/or differentiation of DC precursor cells. The methods of the present invention are conducted by culturing DC precursor cells in media added with multiple cytokines. The multiple cytokines preferably include SCF and interleukin 3 (IL-3), and more preferably, further include FLT-3 ligand (FLT-3L) or interleukin 6 (IL-6). Specifically, media supplemented with all of FLT-3L, SCF, IL-3, and IL-6 can be suitably used to prepare sufficient number of DCs to obtain therapeutic effect, even when the quantity of DCs collected from a patient is small.

More preferably, the methods further comprise a step of culturing in the presence of (i) GM-CSF and IL-4, or (ii) GM-CSF and SCF, after the step of culturing in the medium supplemented with all of FLT-3L, SCF, IL-3, and IL-6. This is effective for efficiently differentiating DC precursor cells into DCs. In other words, even when the quantity of DCs collected from a patient is small, it is possible to efficiently prepare sufficient number of DCs to produce therapeutic effect.

Herein, a dendritic cell (DC) is a cell which takes a dendritic morphology in the mature state and has the ability to activate T cells by presenting an antigen. Herein, a dendritic cell precursor cell is a cell that differentiates into DC in the presence of an appropriate cytokine (specifically, G-CSF, GM-CSF, TNF-α, IL-4, IL-13, SCF (c-kit ligand), Flt-3 ligand, or a combination thereof), and preferably is a cell that can differentiate into a dendritic cell in four weeks or less, more preferably in 20 days or less, even more preferably in 18 days or less, and still more preferably in 16 days or less. Such cells include CD34$^+$ stem cells, hematopoietic progenitor cells, and bone marrow mononuclear cells. These cells can be prepared, for example, as a cell fraction. A cell fraction is a cell population obtained by separation (or fractionation) of cells. A cell fraction may be a composition comprising cells and a pharmaceutically acceptable carrier. Carriers include desired solutions in which viable cells can be suspended, such as physiological saline, phosphate-buffered saline (PBS), culture media, and sera. Differentiation into dendritic cells may be carried out, for example, by culturing for about three days in the presence of SCF (50 ng/ml), GM-CSF (500 U/ml), and TNF-α (50 ng/ml) followed by culture in the presence of SCF (50 ng/ml), GM-CSF (500 U/ml), IL-4 (250 U/ml), and TNF-α (50 ng/ml), more preferably, in the presence of GM-CSF (20 ng/ml) and IL-4 (20 ng/ml), or in the presence of GM-CSF (20 ng/ml) and SCF (10 ng/ml).

Dendritic cells include groups of bone marrow-derived cells with dendrites distributed in various tissues and organs in the body, groups of cells with dendrites distributed in various organs and tissues in the body that result from in vitro differentiation using cytokines or such from bone marrow- or blood-derived stem cells and equivalent cells. Specifically, the dendritic cells include, for example, lymphocytic dendritic cells (including cells which induce Th2 or immune tolerance), bone marrow dendritic cells (generally used dendritic cells, including immature and mature dendritic cells), Langerhans cells (dendritic cells important as antigen-presenting cells in the skin), interdigitating cells (distributed in the lymph nodes and spleen T cell region, and believed to function in antigen presentation to T cells), and follicular dendritic cells (important as antigen-presenting cells for B cells; the cells present antigens to B cells by presenting antigen-antibody complexes or antigen-complement complexes on the surface via the antibody receptor or the complement receptor). Preferably, the dendritic cells highly express MHC class I and class II, and more preferably express CD11c. DCs or DC precursor cells derived from cells collected from bone marrow or peripheral blood are more preferably used in the present invention. The species from which DCs are derived are not particularly limited, and may be mammals, including primates such as humans and monkeys, rodents such as mice and rats, as well as rabbits, bovines, and goats.

A dendritic cell may also be a cell with dendritic morphology and that is positive for two or more surface markers selected from the group consisting of CD11c, HLA-class II (HLA-DR, -DP, or -DQ), CD40, and CD1a. The dendritic cell of the present invention is more preferably an HLA-class II$^+$ and CD11c$^+$ cell, even more preferably, a CD1a$^+$, HLA-class II$^+$, and CD11c$^+$ cell that is negative in lineage markers (Lin$^-$), i.e, that is devoid of the expression of T cell marker (CD3), B cell markers (CD19, CD20), NK cell marker (CD56), neutrophil marker (CD15), and monocyte marker (CD14). When the cells are myeloid dendritic cells (myeloid DCs), they preferably also express CD11b. For example, CD11b$^+$, CD11c$^+$ cells are included in the DCs of the present invention. When the cells are lymphoid dendritic cells (lymphoid DC), they may also express CD8.

In addition, the dendritic cells of the present invention include both mature and immature dendritic cells. "Immature dendritic cells" refers to dendritic cells having significantly low T cell-activating ability as compared with in a mature state. Specifically, the immature dendritic cells may have an antigen-presenting ability that is lower than ½, preferably lower than ¼ of that of dendritic cells which maturation had been induced by adding LPS (1 μg/ml) and culturing for two days. The antigen-presenting ability can be quantified, for example, using the allo T cell-activating ability (mixed lymphocyte test: allo T cells and dendritic cells are co-cultured at a T cell:dendritic cell ratio of 1:10, or preferably at varied ratios; 3H-thymidine is added 8 hours before terminating cultivation, and the T cell growth capacity is assessed based on the amount of $^3$H-thymidine incorporated into the DNA of the T cells (see Gene Therapy 7; 249-254 (2000)). Alternatively, it can be assessed by testing the ability to induce specific cytotoxic T cells (CTLs) using a peptide, in which a known class I-restricted peptide of a certain antigen is added to dendritic cells; the dendritic cells are co-cultured with T cells obtained from peripheral blood of the same healthy donor from whom the dendritic cells had been collected (with 25 U/ml or preferably 100 U/ml of IL-2 on day 3 or later). The T cells are preferably stimulated with dendritic cells three times during 21 days, more preferably stimulated with dendritic cells twice during 14 days. The resulting effector cells are co-cultured for four hours with $^{51}$Cr-labeled target cells (class I-restricted peptide positive tumor cells) at a ratio of 100:1 to 2.5:1 (100:1, 50:1, 25:1, 20:1, 12.5:1, 10:1, 5:1, or 2.5:1), preferably at a ratio of 10:1; and $^{51}$Cr released from the target cells is quantified (see Arch Dermatol Res 292:325-332 (2000)). Furthermore, the immature dendritic cells preferably have phagocytic ability for antigens, and more preferably show low (for example, significantly low as compared to mature DCs induced by LPS as described above) or negative expression of receptors that induce the costimulation for T cell activation. On the other hand, "mature dendritic cells" refers to dendritic cells that have significantly strong antigen-presenting ability for T cell activation or the like as compared with in the immature state. Specifically, the mature dendritic cells may have an antigen-presenting ability that is half or stronger, preferably equivalent to or stronger than the antigen-presenting ability of dendritic cells in which maturation has been induced by adding LPS (1 µg/ml) and culturing for two days. Furthermore, the mature dendritic cells preferably have weak or no phagocytic ability for antigen, and more preferably are positive for the expression of receptors that induce the costimulation for T cell activation. The activation of dendritic cells refers to the transition from immature to mature dendritic cell; and the activated dendritic cells encompass mature dendritic cells and dendritic cells in the process of the transition, wherein the expression of CD80 and CD86 that induce costimulatory signals are elevated by the activating stimuli.

Mature human dendritic cells are cells that are positive for the expression of CD40, CD80, CD86, and HLA-class II. An immature dendritic cell can be distinguished from a mature dendritic cell, for example, based on markers selected from the group consisting of CD80 and CD86. An immature dendritic cell is weakly positive and preferably negative for these markers, while a mature dendritic cell is positive.

As described above, immature dendritic cells generally have a high phagocytic ability. When dendritic cells are added with LPS (1 µg/ml) and cultured for two days, they become activated and their phagocytic ability is reduced. The phagocytic ability can be detected by measuring the amount of small molecules taken up into dendritic cells or the proportion of uptaking cells. The phagocytic ability is preferably determined by the amount of small molecules taken up into dendritic cells. For example, using colored beads with a diameter of about 1 µm, the uptake of beads into dendritic cells can be measured. Quantitation is performed by subtracting the positive background at 4° C. A high phagocytic ability indicates an ability wherein the amount of small molecules taken up into dendritic cells is 4 times or more, more preferably 5 times or more, and even more preferably 6 times or more than that taken up into dendritic cells stimulated with LPS (1 µg/ml) for two days as described above. Alternatively, the proportion of cells taking up small molecules is twice or more, and more preferably 3 times or more. A low phagocytic ability is indicated when the amount of small molecules taken up into dendritic cells is less than four times, more preferably less than twice, and more preferably less than 1.5 times to that taken up into dendritic cells stimulated with LPS (1 µg/ml) for two days. Alternatively, when measured as the proportion of cells that take up small molecules, the proportion is less than twice, and more preferably less than 1.5 times.

Discrimination of mature dendritic cells is routinely performed by those skilled in the art, and the respective markers described above and methods for measuring their expression are also well known to those skilled in the art. For example, CD11c is an adhesion glycoprotein of about 150 kD (p150, integrin α chain). CD11c binds to CD18 to form a CD11c/CD18 complex, which is capable of binding to fibrinogen and has been reported to function as a receptor for iC3b and ICAM-1. In addition, it has been reported that CD11c/CD18 can function as an adhesion molecule that binds to receptors on stimulated epithelia (Knapp, W. et al., eds., 1989, Leucocyte Typing IV: White Cell Differentiation Antigens, Oxford University Press, New York; Barclay, N. A. et al., eds., 1993, The Leucocyte Antigen Facts Book, CD11 Section, Academic Press Inc., San Diego, Calif., p. 124; Stacker, S. A. and T. A. Springer, 1991, J. Immunol. 146:648).

CD1a is a polypeptide of about 49 kD, which binds to β2 microglobulin. CD1a is structurally similar to an MHC class I antigen and is assumed to function in antigen presentation (Knapp, W. et al., eds., 1989, Leucocyte Typing IV: White Cell Differentiation Antigens, Oxford University Press, New York; Schlossman, S. et al., eds., 1995, Leucocyte Typing V: White Cell Differentiation Antigens. Oxford University Press, New York; Hanau, D. et al., 1990, J. Investigative Dermatol. 95: 503; Calabi, F. and A. Bradbury., 1991., Tissue Antigens 37: 1).

CD11b is also referred to as integrin αM chain, Mac-1, CR3, iC3bR (complement receptor type 3), or Mo1, and is a type I transmembrane glycoprotein with a molecular weight of about 165 to 170. CD11b functions as a receptor for complement (iC3b), fibrinogen, and coagulation factor X, and is involved in phagocytosis (Todd R. F. et al. J. Immunol., 126, 1435-1442 (1981); Leong A. S. Y. Appl. Immunohistochem. Surg. Pathol., 120-128 (1993); Todd R. F. et al. Hybridoma, 1, 329-337 (1982); Cobbold S. et al. Leucocyte Typing III, 788-803 (1987); Keizer G et al. Eur. J. Immunol., 15, 1142-1148. (1985); Laffon A. et al. J. Clin. Invest., 88, 546-552 (1991); Acevedo A. et al. J. Invest. Dermatol., 97, 659-666 (1991)).

CD11c (integrin αX subunit, or p150 leukocyte surface antigen) is a molecule of the integrin family, and like other leukocyte integrins (CD11a, CD11b, and CD11d), it binds to the integrin β2 subunit (CD18) non-covalently. CD11c is a transmembrane glycoprotein with a molecular weight of 145 to 150 kDa, and is well known as a dendritic cell marker (Molica S. et al. Blood, 81, 2466 (1993); Van der Vieren M. et al. Immunity, 3, 683-690 (1995); Hogg N. et al. Leucocyte Typing III, 576-602 (1987)).

CD14 is a glycosylphosphatidylinositol (GPI)-anchored single-chain glycoprotein of 53 to 55 kD expressed in dendritic reticulum cells and some types of Langerhans cells. CD14 was identified as a surface receptor having high affinity to a complex of LPS and serum LPS-binding protein (LPB) (McMichael, A. J. et al., eds., 1987, Leucocyte Typing III: White Cell Differentiation Antigens, Oxford University Press, New York; Knapp, W. et al., eds., 1989, Leucocyte Typing IV: White Cell Differentiation Antigens, Oxford University Press, New York; Schlossman, S. et al., eds., 1995, Leucocyte Typing V: White Cell Differentiation Antigens. Oxford University Press, New York; Wright, S. D. et al., 1990, Science 249:1434).

CD40 is a type I integral membrane protein of 45 to 48 kD (type I integral membrane glycoprotein). CD40 is frequently used as a cell marker (Schlossman, S. et al., eds., 1995, Leucocyte Typing V: White Cell Differentiation Antigens. Oxford University Press, New York; Galy, A. H. M.; and H. Spits, 1992, J. Immunol. 149: 775; Clark, E. A. and J. A. Ledbetter, 1986, Proc. Natl. Acad. Sci. 83: 4494; Itoh, H. et al., 1991, Cell 66: 233; Barclay, N. A. et al., 1993, The Leucocyte Antigen Facts Book., Academic Press).

CD80 is a transmembrane glycoprotein of about 60 kD, and is a member of the Ig supergene family. CD80 is a ligand for CD28 and CD152 (CTLA-4) expressed in T cells (Schlossman, S. et al., eds., 1995, Leucocyte Typing V: White Cell Differentiation Antigens. Oxford University Press, New York; Schwarts, R. H., 1992, Cell 71: 1065; Azuma, M. et al., 1993, J. Exp. Med. 177: 845; Koulova, L. et al., 1991, J. Exp. Med. 173: 759; Freeman, G. J. et al., 1998, J. Immunol. 161: 2708; Behrens, L. et al., 1998, J. Immunol., 161(11):5943; Guesdon, J.-L. et al., 1979, J. Histochem. Cytochem. 27: 1131-1139).

CD83 is a transmembrane protein of about 45 kD, and is a member of the Ig superfamily. CD83 has a short extracellular domain of V-type Ig and a C-terminal cytoplasmic tail. CD83 is mainly expressed in follicular dendritic cells, circulating dendritic cells, interdigitating dendritic cells in lymphatic tissues, in vitro-produced dendritic cells, and dendritic cells of the thymus (Zhou, L-J., and T. F. Tedder, 1995, J. Immunol. 154. 3821; Zhou, L-J. et al., 1992, J. Immunol. 149: 735; Summers, K. L. et al., 1995, Clin Exp. Immunol. 100:81; Weissman, D. et al., 1995, Proc. Natl. Acad. Sci. USA. 92: 826; Hart, D. N. J., 1997, Blood 90: 3245).

CD86 (B70/B7-2) is a cell surface protein of about 75 kD, which is a second ligand for CD28 and CTLA-4 and plays an important role in costimulation of T cells in early immune response (Azuma M. et al., 1993, Nature 366: 76; Nozawa Y. et al., 1993, J. Pathology 169: 309; Engle, P. et al. 1994., Blood 84: 1402; Engel, P. et al., CD86 Workshop Report. In: Leukocyte Typing V. Schlossman, S. F. et al. eds., 1994, Oxford University Press; Yang, X. F. et al., 1994, Upregulation of CD86 antigen on TPA stimulated U937 cells, 1994, (abstract). American Society of Hematology, Nashville, Tenn.; Guesdon, J.-L. et al., 1979, J. Histochem. Cytochem. 27: 1131-1139).

CCR7 is also called BLR-2, EBI-1, and CMKBR7, which is a seven-transmembrane G protein-coupled receptor, and is a receptor of the CC chemokines, MIP-3β/Exodus 3/ELC/CCL19 and 6Ckine/Exodus 2/SLC/TCA4/CCL21 (Sallusto, F. et al., 1999, Nature 401:708-12; Lipp, M. et al., 2000, Curr. Top. Microbiol. Immunol. 251:173-9; Birkenbach, M. et al., 1993, J. Virol. 67:2209-20; Schweickart, V. L. et al., 1994, Genomics 23:643-50; Burgstahler, R. et al., 1995, Biochem. Biophys. Res. Commun. 215:737-43; Yoshida, R. et al., 1997, J. Biol. Chem. 272:13803-9; Yoshida, R. et al., 1998, J. Biol. Chem. 273:7118-22; Yoshida, R. et al., 1998, Int. Immunol. 10:901-10; Kim, C. H. et al., 1998, J. Immunol. 161:2580-5; Yanagihara, S. et al., 1998, J. Immunol. 161:3096-102).

DR, DP, and DQ exist as HLA-class II, and can be collectively detected using antibodies that bind to all of these (Pawelec, G et al., 1985, Human Immunology 12:165; Ziegler, A. et al., 1986, Immunobiol. 171:77). HLA-DR is one of the human MHC class II antigens, which is a transmembrane glycoprotein consisting of an α chain (36 kDa) and a β subunit (27 kDa). In epidermal Langerhans cells, it is co-expressed with CD1a antigen. CD1a plays a principal role in cell interaction for antigen presentation (Barclay, N. A. et al., 1993, The Leucocyte Antigen Facts Book. p. 376. Academic Press).

Dendritic cells of humans and nonhuman mammals can be specified using products of the above-described marker genes and homologous genes thereof as an indicator. Antibodies for such markers are available, for example, from BD Biosciences (BD PharMingen), and detailed information is, available at the company website or its distributor websites.

For dendritic cell markers, also see the references by Kiertscher et al. and Oehler et al. (Kiertscher S M, Roth M D, Human CD 14$^+$ leukocytes acquire the phenotype and function of antigen-presenting dendritic cells when cultured in GM-CSF and IL-4, J. Leukoc. Biol., 1996, 59(2):208-18; Oehler, L. et al., Neutrophil granulocyte-committed cells can be driven to acquire dendritic cell characteristics., J. Exp. Med., 1998, 187(7):1019-28). Regarding flow cytometry, see the references by Okano et al. and Stites et al. (Okano, S. et al., Recombinant Sendai virus vectors for activated T lymphocytes. Gene Ther., 2003, 10(16):1381-91; Stites, D. et al., Flow cytometric analysis of lymphocyte phenotypes in AIDS using monoclonal antibodies and simultaneous dual immunofluorescence., Clin. Immunol. Immunopathol., 1986, 38:161-177). The expression of each of the markers may be determined, for example, using as a threshold the fluorescence intensity that makes a positive rate of 1% or less when stained with an isotype control antibody, wherein the fluorescence equal to or above the threshold is deemed positive, and the fluorescence below deemed negative.

Dendritic cells or precursor cells thereof can be prepared according to or based on known methods. For example, the cells can be isolated from blood (for example, peripheral or cord blood), bone marrow, lymph nodes, other lymphatic organs, spleen, and skin (Bishop et al., Blood 83: 610-616, 1994; Bontkes, H. J. et al. (2002) J. Leukoc. Biol. 72, 321-329; Katsuaki, S. et al. (1998) CRYOBIOLOGY 37, 362-371; Ladan, K. et al. (2006) Stem Cells 24, 2150-2157; Ueda, T. et al. (2000) J. Clin. Invest. 105: 1013-1021). Dendritic cells to be used in the context of the present invention are preferably obtained from blood or bone marrow. Alternatively, dendritic cells to be used in the present invention may be skin Langerhans cells, veiled cells of afferent lymphatics, follicular dendritic cells, spleen dendritic cells, and interdigitating cells of lymphatic organs. The dendritic cells used in the present invention include dendritic cells selected from the group consisting of CD34$^+$-derived dendritic cells, bone marrow-derived dendritic cells, monocyte-derived dendritic cells, splenic cell-derived dendritic cells, skin-derived dendritic cells, follicular dendritic cells, and germinal center dendritic cells. In particular, preferred DC precursor cells are hematopoietic stem cells, hematopoietic progenitor cells, and the like, obtained from bone marrow or peripheral blood. Hematopoietic stem cells or hematopoietic progenitor cells can be isolated by negative selection using commercially available kits or such, or by positive selection using CD34$^+$ or such (see U.S. patent application Ser. No. 08/539,142). For example, cell isolation methods that use surface antigens by magnetic beads, fluorescent label sorting, biotin-avidin binding carriers, and such are known (Berenson et al., J. Immunol. Meth., 91:11, 1986; WO 93/08268).

When DCs or DC precursor cells are selected (or enriched) from a composition including DCs or DC precursor cells and other cells, it is preferable to perform so-called negative selection which removes cells other than the DCs or DC precursor cells. Through the negative selection process, precursors of DC-granulocytes (J. Exp. Med., 1998, 187: 1019-

1028; Blood, 1996, 87: 4520-4530) remain without being removed and thus, it is considered that not only DCs differentiated from adherent CD14$^+$ cells but also DCs differentiated from precursors can be recovered together. This is expected to reduce the cytotoxicity that occurs, for example, when vectors are introduced into DCs.

For example, by removing T cells, NK cells, B cells, and the like, using antibodies specific thereto, DCs can be enriched. Specifically, for example, it is preferable to obtain cells with low or negative expression of a surface marker selected from CD2, CD3, CD8, CD19, CD56, and CD66b, or any combinations thereof. More preferred are cells in which the expressions of CD2, CD3, CD8, CD19, CD56, and CD66b are all low or negative. Therefore, it is preferable to remove cells expressing these markers using antibodies against the markers (Hsu et al., Nature Med. 2:52 (1996)). The negative selection can be performed using polyvalent antibodies. Alternatively, a similar selection can also be performed using beads or the like for magnetic cell separation (MACS). The use of beads is preferred for large scale cell preparation, such as collection of mononuclear cells through blood cell separation or the like. For example, DC precursor cells prepared by negative selection from monocytes that were enriched from a cell solution obtained from the body can be suitably used in the context of the present invention.

Specific methods for isolating dendritic cells are described in, for example, Cameron et al., Science 257:383 (1992); Langhoff et al., Proc. Natl. Acad. Sci. USA 88:7998 (1991); Chehimi et al., J. Gen. Virol. 74:1277 (1993); Cameron et al., Clin. Exp. Immunol. 88:226 (1992); Thomas et al., 1993, J. Immunol. 150:821 (1993); and Karhumaki et al., Clin. Exp. Immunol. 91:482 (1993). The isolation of dendritic cells by flow cytometry is described in, for example, Thomas et al., J. Immunol. 153:4016 (1994); Ferbas et al., J. Immunol. 152: 4649 (1994); and O'Doherty et al., Immunology 82:487 (1994). In addition, magnetic cell separation is described in, for example, Miltenyi et al., Cytometry 11: 231-238 (1990).

Furthermore, for example, human dendritic cells may be isolated and proliferated using the methods described in Macatonia et al., Immunol. 74:399-406 (1991); O'Doherty et al., J. Exp. Med. 178:1067-1078 (1993); Markowicz et al., J. Clin. Invest. 85:955-961 (1990); Romani et al., J. Exp. Med. 180:83-93 (1994); Sallusto et al., J. Exp. Med. 179:1109-1118 (1994); Berhard et al., J. Exp. Med. 55:1099-1104 (1995); and the like. Moreover, dendritic cells can be formed from CD34$^+$ cells obtained from bone marrow, cord blood, peripheral blood, or the like and from peripheral blood-derived mononuclear cells by the method described in Van Tendeloo et al., Gene Ther. 5:700-707 (1998).

DC precursor cells are expanded in a medium containing one or more cytokines. For example, DC precursor cells can be expanded over about ten days even with IL-3 alone. However, expansion over a longer period is not seen with IL-3 alone. The present inventors discovered that by culturing DC precursor cells in a medium containing SCF and IL-3, cells having the ability to differentiate into DCs can be efficiently expanded. Thus, for expansion for two weeks or longer, IL-3 and SCF are preferably used in combination. In particular, DC precursor cells having a strong ability to differentiate into DCs can be obtained in large quantities by culturing DC precursor cells in a medium containing the following four types of cytokines: FLT-3L, SCF, IL-3, and IL-6. The present invention relates to methods for producing DCs, which comprise the step of expanding DC precursor cells in a medium containing IL-3 and SCF but not FLT-3L and IL-6; a medium containing FLT-3L, SCF, and IL-3 but not IL-6; or a medium containing SCF, IL-3, and IL-6 but not FLT-3L. The present invention also relates to methods for producing DCs, which comprise the step of expanding DC precursor cells in a medium containing FLT-3L, SCF, IL-3, and IL-6; for example, a medium containing these cytokines but not a significant amount of one or more cytokines (or any combination thereof) selected from G-CSF, GM-CSF, IL-4, and TNF-α.

FLT-3L (Fms-like tyrosine kinase 3 ligand) is a ligand for Flt-3, and promotes the differentiation and proliferation of hematopoietic precursor cells (Namikawa R. et al., BLOOD 87: 1881-1890 (1996)). The group of polypeptides described in EP 0627487 A2 and WO 94/2839 are included in the Flt-3L of the present invention. Human FLT-3L cDNA is available under the accession number ATCC 69382 from American Type Culture Collection (ATCC). SCF is also referred to as c-kit ligand, mast cell growth factor (MGF), or steel factor (Zsebo et al., Cell 63: 195-201 (1990); Huan, E. Cell 63: 225-233; Williams, D. E., Cell 63: 167-174 (1990); Toksoz. D et al, PNAS 89: 7350-7354 (1992)). SCF includes the polypeptides described in EP 423,980.

IL-3 is a hematopoietic factor produced by activated T cells, mast cells, and eosinophils. IL-3 of the present invention includes the IL-3 polypeptides described in U.S. Pat. No. 5,108,910. A DNA sequence encoding the human IL-3 protein is available under the accession number ATCC 67747. IL-6 was discovered as a B cell differentiation-inducing factor. IL-6 has pleiotropic physiological activities in addition to those involved in the antibody production system, such as induction of biosynthesis of acute-phase proteins in the liver and promotion of hematopoietic stem cell proliferation based on the synergistic effect with IL-3 (Paul S R et al., Blood, 1991, 77: 1723-1733). IL-4 is produced mainly by helper T cells, and has broad physiological activities on T cells, B cells, and other blood cells (Mosley et al., Cell 59: 335 (1989); Idzerda et al., J. Exp. Med. 171: 861 (1990); Galizzi et al., Intl. Immunol. 2: 669 (1990)). GM-CSF is a cytokine that was isolated as a factor that stimulates the growth of colonies containing macrophages or granulocytes (U.S. Pat. Nos. 5,108,910 and 5,229,496). GM-CSF is an essential factor for growth and development of precursor cells of granulocytes and macrophages, and stimulates myeloblasts and monoblasts to induce their differentiation.

The concentration of each cytokine may be appropriately adjusted; however, the concentration of FLT-3L is 5 to 35 ng/ml, preferably 10 to 30 ng/ml, more preferably 15 to 25 ng/ml, and still more preferably about 20 ng/ml. For example, when GM-CSF-free media such as FS36 are used, the concentrations of SCF, IL-3, and IL-6 are 3 to 20 ng/ml, preferably 5 to 15 ng/ml, more preferably 7 to 12 ng/ml, and still more preferably about 10 ng/ml, but are not limited thereto. For example, RPMI1640 and IMDM can be used as medium. The medium is appropriately supplemented with 5 to 20% serum, preferably about 10% serum, preferably fetal bovine serum (FBS). Culture of DC precursor cells can be started with about $1 \times 10^5$ to $5 \times 10^5$ cells, for example, about $2.5 \times 10^5$ cells. Preferably, the cells are passaged every three or four days. The cell count is preferably adjusted to $2 \times 10^6$ cells/ml or a lower concentration at upon passaging. When primate CD34$^+$ cells such as human CD34$^+$ cells are cultured in the presence of the combination of GM-CSF and SCF, GM-CSF may be used, for example, at 1 to 500 ng/ml (1 to 200 ng/ml or 1 to 100 ng/ml), preferably 2 to 300 ng/ml, for example, 5 to 200 ng/ml, more preferably 10 to 150 ng/ml, even more preferably 20 to 120 ng/ml, and still more preferably 30 to 100 ng/ml. SCF may be used, for example, at 0.5 to 500 ng/ml (0.5 to 100 ng/ml or 0.5 to 50 ng/ml), preferably 1 to 300 ng/ml, more preferably 2 to 200 ng/ml, even more preferably 5 to 100 ng/ml, for example, 10 to 70 ng/ml, still more preferably, for example, 20 to 60 ng/ml, and yet more preferably about 25 to 50 ng/ml or so.

The present inventors found that, by adjusting the period of DC precursor cell expansion to about three to four weeks, the efficiency of subsequent differentiation into DCs can be markedly increased. Longer culture period yields more cells but reduces the efficiency of differentiation into DCs. In particular, the efficiency of differentiation into DCs is markedly reduced with DC precursor cells expanded for five weeks in FS36 medium. Accordingly, if a GM-CSF-free medium, for example, FS36 is used, the period of DC precursor cell culture is about three to about four weeks, preferably about three weeks, for example, 18 to 24 days, and more preferably 20 to 22 days; and it is preferable to avoid expansion of DC precursor cells for a longer period in a medium containing the same combination of cytokines. After culturing for these periods, DCs are cultured and differentiated in a DC differentiation medium as described below. For example, when DC precursor cells are cultured in a medium containing FLT-3L, SCF, IL-3, and IL-6, after culturing for the period indicated above, they are cultured in a medium other than one that contains all of FLT-3L, SCF, IL-3, and IL-6.

The expanded DC precursor cells can be differentiated into DCs using cytokines. For example, they can be differentiated using granulocyte-colony stimulating factor (G-CSF), GM-CSF, tumor necrosis factor (TNF)-α, IL-4, IL-13, SCF (c-kit ligand), Flt-3 ligand, or a combination thereof. For example, DC precursor cells expanded in a GM-CSF-free medium (such as FS36) are preferably differentiated into DCs in the presence of GM-CSF and IL-4 or in the presence of GM-CSF and SCF. They can also be differentiated into mature dendritic cells by further stimulation with TNF-α. In the present invention, DC precursor cells expanded in a GM-CSF-free medium (such as FS36) according to the method described above are preferably cultured in the presence of (i) GM-CSF and IL-4, or (ii) GM-CSF and SCF. The cytokine concentration may be appropriately adjusted; however, when DC precursor cells are expanded using a GM-CSF-free medium, the concentrations of GM-CSF and IL-4 are, for example, 1 to 500 ng/ml, more specifically 2 to 300 ng/ml, for example, 5 to 100 ng/ml, preferably 10 to 50 ng/ml, more preferably 15 to 25 ng/ml, and still more preferably about 20 ng/ml. The concentration of SCF is, for example, 1 to 200 ng/ml, more specifically, 2 to 100 ng/ml, 2 to 80 ng/ml, or 2 to 60 ng/ml, more specifically, for example, 3 to 20 ng/ml, preferably 5 to 15 ng/ml, more preferably 7 to 12 ng/ml, and still more preferably about 10 ng/ml. For example, RPMI1640 and IMDM can be used as medium. The medium is appropriately supplemented with 5 to 20%, preferably about 10% serum, preferably fetal bovine serum (FBS). The culture period is, for example, five to 15 days, preferably six to ten days, and more preferably about seven days. When the cells are expanded in FS36, DCs can be obtained more efficiently by differentiation in the presence of GM-CSF and SCF rather than in the presence of GM-CSF and IL-4.

Furthermore, human DC precursor cells such as human CD34$^+$ cells, or DC precursor cells from other primates can be expanded and differentiated at the same time by culturing in the presence of (i) GM-CSF and IL-4, or (ii) GM-CSF and SCF, without any expansion using SCF and IL-3 (S3), or FS36 as described above. In this case, the culture period is one to ten weeks, for example, one to six weeks, preferably two to five weeks, three to six weeks, three to five weeks, or four to five weeks. Primate CD34$^+$ cells that can be used include, for example, cord blood-derived CD34$^+$ cells, bone marrow-derived CD34$^+$ cells, and peripheral blood-derived CD34$^+$ cells.

It is possible to use an appropriate desired medium as culture solution. Such culture solution includes, for example, DMEM (Dulbecco's Modified Eagle Medium), MEM (Minimum Essential Medium), RPMI-1640, X-VIVO™ (Lonza), and IMDM (Iscove's Modified Dulbecco's Medium). IMDM is used most preferably. Preferably, the media are appropriately supplemented with serum, for example, at 1 to 20% (v/v), more preferably 2 to 20%, even more preferably 5 to 15%, and still more preferably 5 to 10% (for example, about 10%). The serum is preferably bovine-derived serum, and most preferably fetal calf serum (FCS). When iDCs are expanded from human CD34$^+$ cells, it is preferable that TNF-α and/or IL-4 are not added. For example, the concentrations of TNF-α and IL-4 in the medium are preferably in a range that does not significantly exceed their concentrations in the serum to be added. For example, the concentrations are preferably three times, two times, one time or lower than the cytokine concentrations in the serum (for example, normal FCS), and are preferably one half or lower, more preferably one third or lower, or one fifth or lower, specifically 50 ng/ml or lower, preferably 40, 30, 20, 10, 5, 3, or 1 ng/ml, or lower. The medium for expanding iDCs from human CD34$^+$ cells is preferably supplemented only with GM-CSF and SCF as cytokines. The medium preferably contains only GM-CSF and SCF as cytokines, and no other cytokines.

The present invention provides compositions for expanding dendritic cells, compositions for preparing dendritic cells, compositions for producing dendritic cells, media for expanding dendritic cells, media for preparing dendritic cells, and media for producing dendritic cells, all of which comprise GM-CSF and SCF. The compositions may appropriately comprise sterilized water, buffers, salts, and the like. The culture media include the culture solutions described above, but are not limited thereto. The media may or may not contain sera. Further, the media may or may not contain antibiotics. The present invention also relates to the use of GM-CSF and SCF in the production of these compositions and media. The present invention also relates to kits for expanding dendritic cells, kits for preparing dendritic cells, and kits for producing dendritic cells, all of which comprise GM-CSF and SCF as components. The kits may further comprise culture solutions (for example, not containing serum) or powder for preparing culture solutions (containing amino acids, salts, and the like, but not containing any serum, antibiotic, and such). Preferably, these compositions, media, and kits are intended for expanding, preparing, and producing primate dendritic cells including human dendritic cells, and more preferably, for expanding, preparing, and producing dendritic cells from primate CD34$^+$ cells including human CD34$^+$ cells. Preferably, they do not contain TNF-α and/or IL-4. For example, the concentrations of TNF-α and IL-4 in the composition and medium are preferably in a range that does not significantly exceed their concentrations in the serum when serum is added. For example, the concentrations are preferably three times, two times, one time or lower than the cytokine concentrations in the serum (for example, normal FCS), and are preferably one half or lower, more preferably one third or lower, or one fifth or lower, specifically 50 ng/ml or lower, preferably 40, 30, 20, 10, 5, 3, or 1 ng/ml, or lower. When serum is not added, preferably only GM-CSF and SCF are included as cytokines.

According to the methods of the present invention, DCs can be expanded from CD34$^+$ cells by, for example, $10^2$ times, preferably $0.5 \times 10^3$ times, more preferably $1 \times 10^3$ times, even more preferably $0.5 \times 10^4$ times, still more preferably $1 \times 10^4$ times, yet more preferably $0.5 \times 10^5$ times, even still more preferably $1 \times 10^5$ times, and still yet more preferably $0.5 \times 10^6$ times or more. For example, with one week-culture, the cells can be increased at a rate of five times, preferably 6, 7, 8, 9, 10, 11, 12, or 13 times or higher. The expanded cells contain a high purity of DCs (iDCs). The percentage of CD11c-positive cells in the expanded cells (the ratio of CD11c$^+$ cells in the total cells) is, for example, 30% or higher, preferably 40% or higher, more preferably 50% or higher, 60% or higher, 70% or higher, 75% or higher, 80% or higher, or 85% or higher. Furthermore, mature DCs can be obtained by treating iDCs with LPS, Poly(I:C), Sendai virus, or such.

The dendritic cells obtained by the methods of the present invention are useful as DC vaccine which is useful in immunotherapy for infections, cancers, and other diseases of interest for which beneficial effects can be expected from immune induction. For example, in tumor immunotherapy, dendritic cells are made to present tumor antigens by mixing dendritic cells with tumor cell lysates, pulsing with peptides, introducing tumor antigen genes into dendritic cells, or such. The resulting dendritic cells can be used in DC therapy against tumors.

For example, the method of introducing tumor antigen genes into dendritic cells can be expected to prolong the duration of tumor antigen presentation in vivo as compared with tumor lysates and peptide pulses, and also has the advantage of not being limited by HLA (in the case of peptides: a certain peptide derived from an antigen is used; however, due to the requirement of HLA binding, when the HLA type changes, the peptide region used in the antigen also changes).

The liposome method, electroporation, and the like are available to introduce plasmids as vectors for introducing genes into dendritic cells (Cancer Gene Ther 4, 17-25 (1997)). More practical vectors include the following three types of vectors: (i) adenoviral vectors (J. Immunotherapy 25:445-454 (2002); Gene therapy 7:249-254 (2000)); (ii) retroviral vectors (J. Leuko. Biol., 263-267 (1999); Br. J. Haematol. 108: 817-824 (2000)), and (iii) lentiviral vectors (J. Gene Med. 3: 311-320 (2001); J. Immunol. Meth. 153-165 (2002); Mol. Ther., 283-290 (2002); Cancer Gene Therapy 9: 715-724 (2002)). Contact between the vector and dendritic cells can be achieved in vivo or in vitro, for example, in a desired physiological aqueous solution such as culture solution, physiological saline, blood, plasma, serum, or body fluid.

For example, genes can be introduced into CD34 positive stem cells using retroviral vectors such as lentiviral vectors, and then dendritic cells can be obtained in vitro. Alternatively, it is possible to introduce genes into peripheral blood-derived monocytes and differentiated dendritic cells by maintaining vpx (which promotes nuclear translocation of the proviral DNA) in the helper construct in the case of simian immunodeficiency virus (SIV), or by inserting a DNA-flap sequence in the case of HIV (this also promotes nuclear translocation of proviral DNA) (Mol. Ther. 283-290 (2002)).

Meanwhile, the adenovirus is considered promising as a vector for genetic introduction into dendritic cells because of the high introduction efficiency (about 80%) and its ability to directly introduce genes into differentiated dendritic cells (J. Immunotherapy, 25; 445-454 (2002)). However, at MOIs that increase the efficiency of genetic introduction, there is an immunosuppressive effect that decreases the mixed lymphocyte reaction (MLR) of allo T cells (Gene Therapy 7; 249-254 (2000)). Therefore, attention is needed when using high MOIs (in particular, at high DC:T ratios). Furthermore, because of episome dilution, it is preferable to introduce genes at a more differentiated stage, rather than differentiating dendritic cells after introducing genes into stem cells such as CD34-positive cells.

In addition to the virus vectors described above, RNA viruses such as minus-strand RNA viruses can also be suitably introduced into DCs. When minus-strand RNA viral vectors are used, gene transfer is terminated after a very short contact period, and an introduction efficiency of nearly 100% can be achieved. In addition, the degree of suppression of allo T cell response is relatively mild so that the T cell-stimulating ability is maintained (WO 2005/042737). Minus-strand RNA viruses are viruses that contain minus-strand (an antisense strand against the viral protein-encoding sense strand) RNA as the genome and are also referred to as negative-strand RNA viruses. Minus-strand RNA viruses that are used in the present invention include viruses belonging to, for example, the following families: Paramyxovirus (Paramyxoviridae: including the genera Respirovirus, Morbillivirus, Rubulavirus, and Pneumovirus), Rhabdovirus (Rhabdoviridae: including the genera Vesiculovirus, Lyssavirus, and Ephemerovirus), Filovirus (Filoviridae), Orthomyxovirus (Orthomyxoviridae: including Influenza viruses A, B, and C, and Thogoto-like viruses), Bunyavirus (Bunyaviridae: including the genera Bunyavirus, Hantavirus, Nairovirus, and Phlebovirus), and Arenavirus (Arenaviridae).

Minus-strand RNA viruses used in the present invention are preferably viruses belonging to the subfamily Paramyxovirinae (including the genera Respirovirus, Rubulavirus, and Morbillivirus) and derivatives thereof; and more preferably viruses belonging to the genus Respirovirus (also referred to as the genus Paramyxovirus) which includes Sendai viruses, or derivatives thereof. The derivatives include, for example, chemically modified viruses and viruses whose viral genes have been modified in a manner that the gene-transferring ability of the virus is not impaired. For example, F gene-deficient minus-strand RNA viruses are suitable. For various minus-strand RNA viruses, methods for producing recombinant viruses are known (WO 97/16539; WO 97/16538; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci. USA 93: 15400-15404).

The introduction efficiency of the minus-strand RNA viral vectors is significantly higher with dendritic cells in an inactivated state (immature state) than with mature dendritic cells. Thus, minus-strand RNA viral vectors are preferably contacted with immature dendritic cells or mixed with a cell fraction containing immature dendritic cells. Dendritic cells can be activated through contact with bacteria, lipopolysaccharide (LPS), double-stranded RNAs, RNA viruses, or the like. When dendritic cells into which genes are to be introduced are separately activated by such a method, the vector may be introduced after activation. However, to prevent reduction in the efficiency of vector introduction, it is preferable to carry out the activation not before vector introduction, but after the gene has been introduced using the vector (or at the same time when dendritic cells are contacted with the vector).

For example, DC precursor cells expanded by the methods of the present invention are differentiated into DCs by culturing the precursor cells in the presence of GM-CSF and SCF, and then the DCs are activated by culturing in the presence of LPS, RNA viruses, or the like. The culture period may be appropriately adjusted and is, for example, two to seven days.

For example, when used for immunostimulation (e.g., tumor immunity), RNA viruses such as minus-strand RNA viruses can be used for gene transfer, and the RNA virus infection itself induces the activation of dendritic cells. Thus, it is possible to omit the step of activation by cytokine treatment and the like after introduction, which is expected to contribute to maintenance of cell viability, reduction in cost, and further reduction in the time required for ex vivo manipulation. Activated T cells, in particular, tumor specific cytotoxic T cells and the like, which are required for T cell transfer therapy can be efficiently and easily induced ex vivo in a short period by using dendritic cells into which genes have been introduced using RNA viral vectors (WO 2005/042737; WO 2006/001122).

DCs can be appropriately formulated into compositions in combination with pharmaceutically acceptable carriers. Examples of carriers include desired solutions that can be used to suspend viable cells, such as physiological saline, phosphate buffered saline (PBS), culture solutions, and serum. The compositions may comprise antigenic peptides to be presented on dendritic cells. Furthermore, when DCs are used as vaccine, immunostimulants such as cytokines, cholera toxin, and Salmonella toxin may be added to the vaccine compositions to increase immunogenicity. Moreover, the vaccine may be combined with adjuvants, such as alum, incomplete Freund's adjuvant, MF59 (oil emulsion), MTP-PE (muramyl tripeptide derived from cell wall of mycobacteria), and QS-21 (derived from soapbark tree *Quilaja saponaria*).

Antigens can be presented on DCs by mixing DCs with a cell lysate antigen by pulsing peptides, or by introducing an antigen gene-encoding vector into DCs. Antigens include desired antigens related to infectious microorganisms, viruses, parasites, pathogens, cancers, and the like. These may be structural or non-structural proteins. Such antigens (or processed peptides thereof) bind to MHC molecules on the surface of dendritic cells, and are presented on the cell surface, inducing immune responses.

When used as a vaccine, the antigens can be applied to, for example, tumors, infectious diseases, and other general diseases. To treat infectious diseases, for example, epitopes of an antigen protein of an infectious microorganism may be analyzed, and then expressed or presented by dendritic cells.

Antigens derived from pathogens include, for example, proteins of hepatitis A virus, hepatitis B virus, hepatitis C virus, hepatitis delta virus, papilloma virus antigen, herpes simplex virus (HSV), varicella-zoster virus (VZV), Epstein-Barr virus, Cytomegalovirus (CMV), HIV, malaria, and the like, or partial peptides thereof (G. L. Mandell et al. (Ed.) Hinman et al., Principles and Practice of Infectious Diseases, 3rd Ed., Churchill Livingstone Inc., NY, pp. 2320-2333). DCs presenting these antigens can be used prophylactically or therapeutically against the infectious diseases. Specifically, envelopes of influenza highly-virulent strain H5N1 for influenza, envelope proteins of Japanese encephalitis virus (Vaccine, vol. 17, No. 15-16, 1869-1882 (1999)) for Japanese encephalitis, HIV and SIV gag proteins (J. Immunology (2000) vol. 164, 4968-4978), HIV envelope proteins, Nef protein, and other viral proteins for AIDS can be mentioned. In addition, for example, cholera toxin B subunit (CTB) (Arakawa T, et al., Nature Biotechnology (1998) 16(10): 934-8, Arakawa T, et al., Nature Biotechnology (1998) 16(3): 292-7) for cholera; rabies virus glycoprotein (Lodmell D L et al., 1998, Nature Medicine 4(8):949-52) for rabies; and capsid protein L1 of human papilloma virus type 6 (J. Med. Virol, 60, 200-204 (2000)) for cervical carcinoma can be mentioned. Furthermore, it is possible to use JE-E antigen protein of Japanese encephalitis virus (Japanese Patent Application Kokai Publication No. (JP-A) S64-74982 (unexamined, published Japanese patent application), JP-A (Kokai) H01-285498), gD2 protein of human herpes simplex virus (JP-A (Kokai) H05-252965), polypeptides derived from hepatitis C virus (JP-A (Kokai) H05-192160), polypeptides derived from pseudorabies virus (Japanese Patent Kohyo Publication No. (JP-A) H07-502173 (unexamined Japanese national phase publication corresponding to a non-Japanese international publication), and the like. For example, cells derived from patients infected with such pathogenic microorganisms may be analyzed to identify an epitope of an antigen protein presented on antigen-presenting cells (APC) for use. It is also preferable to appropriately select the HLA type and identify an epitope corresponding to the desired HLA type for use.

To specifically promote an immune response against a tumor, one or more tumor antigens are presented on the dendritic cells. Tumor-related antigens can be obtained, for example, by preparing crude tumor cell extracts or by partial purification of antigens ((Cohen et al., Cancer Res. 54: 1055 (1994); Cohen et al., Eur. J. Immunol. 24: 315 (1994); Itoh et al., J. Immunol. 153: 1202 (1994)). The obtained tumor antigens may be further purified, or may be synthesized or expressed as a recombinant peptide.

When purified dendritic cells are pulsed with (exposed to) antigens and made to take in the antigens, the antigens are processed by the DCs and presented on the cell surface (Germain, R. N., Cell 76: 287 (1994)). There are various known methods for pulsing dendritic cells with antigens, and those skilled in the art routinely select appropriate methods according to the antigen to be presented. The present invention provides compositions comprising DCs that are produced by the methods of the present invention and which present antigens, and uses thereof in immunotherapy. To stimulate immune responses, the compositions of the present invention can be administered by injection, continuous infusion, sustained release from implants, or other appropriate techniques. Typically, the compositions comprising dendritic cells are administered together with physiologically acceptable carriers, excipients, or diluents. The ones that do not show any significant toxicity to the administered individual at the dose or concentration used can be used as a carrier and include, for example, physiological saline.

The tumor antigens may be tumor cell-specific antigens (i.e., existing in tumor cells but absent in non-tumor cells) or antigens that are expressed at a higher level in tumor cells than in non-tumor cells of the same type. The immune system is stimulated through the administration of the dendritic cells. When CTL acts as a major effector, a desired intercellular or extracellular tumor antigen can be used. When an antibody is reacted as the effector by using dendritic cells to activate CD4 T cells which triggers the induction of antibody production through B cell activation, it is preferred to use an antigen presented on the cell surface. For example, a cell surface receptor or cell adhesion protein can be used as the antigen. The tumor antigens include, for example, Muc-1 or Muc-1-like mucin tandem repeat peptide that induce ovarian cancer or the like (U.S. Pat. No. 5,744,144); E6 and E7 proteins of human papilloma virus, which cause cervical cancer; melanoma antigens MART-1, MAGE-1, -2, -3, gp100, and tyrosinase; prostate cancer antigen PSA; as well as CEA (Kim, C. et al., Cancer Immunol. Immunother. 47 (1998) 90-96) and Her2neu (HER2p 63-71, p 780-788; Eur. J. Immunol. 2000; 30: 3338-3346).

Dendritic cells that are prepared according to the present invention are useful in effective immunotherapy for cancers and infectious diseases. Immunological sensitization by dendritic cells introduced with a gene of a tumor antigen or infectious disease-related antigen or T cells stimulated with such dendritic cells serves as an effective method for inducing anti-tumor or anti-infectious disease immunity in patients. The present invention also relates to the use of dendritic cells obtained by the present method in the induction of immune response. Specifically, the present invention relates to the use of dendritic cells obtained by the present method in immunotherapy, in particular, for example, in the treatment of tumors or infectious diseases. Furthermore, the present invention relates to the use of dendritic cells obtained by the present method in the production of immunoactivating agents. Specifically, the present invention relates to the use of dendritic cells obtained by the present method in the production of immunotherapeutic agents, in particular, for example, antitumor agents (tumor growth suppressants) or therapeutic agents for infectious diseases.

The cells can also be applied to general diseases. To treat diabetes, for example, a peptide of an insulin fragment can be used as an epitope in type I diabetes patients or animal models thereof (Coon, B. et al., J. Clin. Invest., 1999, 104(2):189-94).

The DC compositions may further comprise soluble cytokine receptors, cytokines, or other immunoregulatory molecules (Schrader, J. W. Mol. Immunol. 28: 295 (1991)). These cytokines can be prepared as separate compositions from the DC compositions, and administered simultaneously, separately, or sequentially with DCs. In addition, by expressing a cytokine in 1-0 dendritic cells, the cells stimulate the immune system, thereby enhancing immune responses against cancers or infectious microorganisms. Thus, dendritic cells introduced with a gene encoding a cytokine are also useful in the treatment of cancers and other diseases for which cytokine therapy is expected to be effective. A dendritic cell introduced with a vector carrying a gene encoding an immunostimulatory cytokine serves as an effective immune inducing agent. For example, immunostimulatory cytokines include interleukins (for example, IL-1α, IL-1β, IL-2, IL-3, IL-4, IL-6, IL-7, IL-8, IL-9, IL-10, IL-12, IL-15, IL-18, IL-19, IL-20, IL-21, IL-23, and IL-27), interferons (for example, IFN-α, IFN-β, and IFN-γ), tumor necrosis factor (TNF), transforming growth factor (TGF)-β, granulocyte colony stimulating factor (G-CSF), macrophage colony stimulating factor (M-CSF), GM-CSF, fusion proteins containing IL-3 and GM-CSF, insulin-like growth factor (IGF)-I, IGF-2, Flt-3 ligand, Fas ligand, c-kit ligand, CD40 ligand (CD40L), and other immunomodulatory proteins (such as chemokines and costimulatory molecules). These can be used alone or in combination.

The amino acid sequences of these cytokines are well known to those skilled in the art. One may refer to: for IL-4, for example, Arai et al. (1989), J. Immunol. 142(1) 274-282; for IL-6, for example, Yasukawa et al. (1987), EMBO J., 6(10): 2939-2945; for IL-12, for example, Wolf et al. (1991), J. Immunol. 146(9): 3074-3081; for IFN-α, for example, Gren et al. (1984) J. Interferon Res. 4(4): 609-617, and Weismann et al. (1982) Princess Takamatsu Symp. 12: 1-22; for TNF, for example, Pennica et al. (1984) Nature 312: 724-729; for G-CSF, for example, Hirano et al. (1986) Nature 324:73-76; and for GM-CSF, for example, Cantrell et al. (1985) Proc. Natl. Acad. Sci. (USA) 82(18): 6250-6254. More specifically, the nucleic acid sequence encoding GM-CSF includes sequences containing the sequences from position 84 to 461 of Accession number NM_000758 (corresponding to position 18 to 144 of the amino acid sequence of NP_000749). The nucleic acid sequence encoding IL-4 includes sequences containing the sequences from position 443 to 829 of Accession number NM_000589 (corresponding to position 25 to 153 of the amino acid sequence of NP_000580). Vectors can be introduced into dendritic cells by designing them to include natural genes encoding these cytokines or mutant genes that still encode functional cytokines due to the degeneracy of genetic code.

Moreover, the genes may be modified to express modified forms of the cytokines. For example, a cytokine that has two forms, precursor and matured forms (for example, those producing active fragments by cleavage of their signal peptides, or by restrictive proteolysis), may be genetically modified to express either the precursor or the matured form. Other modified forms (for example, fusion proteins of an active fragment of a cytokine and a heterologous sequence (for example, heterologous signal peptide)) can also be used.

Dendritic cells are useful for stimulating the patient's own T cells in vivo, and are also useful for stimulating T cells in vitro. The patient's immune system can be stimulated by ex vivo immunotherapy, in which sensitized T cells are administered to the patient. For example, T cells stimulated with dendritic cells can be prepared by contacting T cells with mature dendritic cells presenting an antigen. The antigen to be presented by the dendritic cells may be a protein (or a processed product thereof) expressed from the vector or may be exogenously pulsed into the dendritic cells. The activated T cells induce CTLs.

The present invention also relates to methods for stimulating the immune system using dendritic cells produced by the methods of the present invention. For example, patients affected with infection, cancer, or the like can be treated to stimulate their immune system. These methods comprise the step of administering dendritic cells or T cells. Specifically, the methods comprise the step of administering into a patient a therapeutically effective amount of DCs produced according to the present invention, or T cells stimulated with the DCs. Immunity against a desired antigen can be induced by pulsing dendritic cells with a desired antigen peptide to make them present the antigen. When T cells are contacted with dendritic cells in vitro, it is preferable to collect T cells from the patient and carry out ex vivo administration.

The administration dose of a composition comprising DCs or T cells to a subject varies depending on the disease, patient's weight, age, sex, and symptom, purpose of administration, form of the administered composition, administration method, and the like; however, the dose can be appropriately determined by those skilled in the art. The administration route can be appropriately selected; for example, administration to the affected sites is preferable. In general, the composition can be infused by intramuscular, intraperitoneal, subcutaneous, or intravenous injection, or by direct infusion into lymph nodes. Preferably, the composition is administered to patients by subcutaneous or intraperitoneal injection, or direct infusion into lymph nodes. Patients can be administered typically with $10^5$ to $10^9$ dendritic cells, preferably $10^6$ to $10^8$ cells, and more preferably about $10^7$ cells. The number of administration can be one time, or may be multiple times within the range of clinically acceptable side effects. The subject of administration is not particularly limited, and includes, for example, birds and mammals (humans and non-human mammals), including chickens, quails, mice, rats, dogs, pigs, cats, bovines, rabbits, sheep, goats, monkeys, and humans, and other vertebrates.

Dendritic cells are useful as an antitumor agent. For example, tumor growth can be suppressed by administering, into tumor sites, dendritic cells presenting the tumor antigen. The tumor site refers to tumor and its surrounding area (for example, an area within 5 mm from the tumor, preferably within 3 mm from the tumor). A stronger effect can be obtained by contacting a tumor antigen with the dendritic cells prior to administration of the dendritic cells into tumors. The contact of a tumor antigen with the dendritic cells can be carried out by using a method wherein a tumor cell lysate is mixed with the dendritic cells, a method wherein the dendritic cells are pulsed with a tumor antigen peptide, or a method wherein a tumor antigen gene is introduced into and expressed by the dendritic cells. Furthermore, anti-tumor effects can be expected to increase by treating DCs with IFN-β or a vector carrying an IFN-β gene, or by direct injection into tumors. For example, an RNA viral vector (e.g., a minus-strand RNA viral vector) carrying an IFN-β gene is a superior antitumor agent. A greater anti-tumor effect can be exerted by combining the administration of the dendritic cells introduced with the RNA viral vector and the injection of a vector carrying an IFN-beta gene into tumor sites.

When T cells activated with the dendritic cells are administered, for example, the T cells can be administered at a dose of about $10^5$ to $10^9$ cells, preferably $10^6$ to $10^9$ cells, and more preferably $10^8$ to $10^9$ cells per 1 m$^2$ body surface area by intravenous injection (see Ridell et al., 1992, Science 257: 238-241). The injection can be repeated at desired intervals (for example, monthly). After the administration, recipients may be monitored for any side effects during or after T cell injection, if required. In this case, it is preferred that T cells are obtained from the same patient from whom the dendritic cells have been derived. Alternatively, the T cells may be collected from a patient, while the dendritic cells to stimulate the T cells may be derived from an HLA-compatible healthy donor. Conversely, the dendritic cells may be collected from a patient, while the T cells may be derived from an HLA-compatible healthy donor.

Cells containing the dendritic cells as the active ingredient of vaccines that are produced according to the present invention are inoculated as therapeutic vaccines to the human body. Thus, the growth capacity can be made deficient to increase safety. For example, it is known that the growth capacity of cord blood-derived monocytes is extremely reduced after the induction of differentiation. However, to use the cells as safer cell vaccines, the growth capacity can be eliminated without losing the vaccine function by treating the cells with heat, radiation, mitomycin C (MMC), or the like. For example, when X-ray irradiation is used, X-ray can be irradiated at a total radiation dose of 1000 to 3300 Rad. With regard to the mitomycin C treatment, mitomycin C can be added to the dendritic cells at a concentration of 25 to 50 µg/ml and incubated at 37° C. for 30 to 60 minutes. When the cells are treated with heat, for example, the cells can be subjected to a heat treatment of 50 to 65° C. for 20 minutes.

EXAMPLES

Hereinbelow, the present invention is specifically described with reference to the Examples; however, it is not to be construed as being limited thereto. All publications cited herein are incorporated as part of this description.

In Examples 1, 2, 4, and 5 described below and in the drawings related to these Examples, the FS36 administration group, GMSCF administration group, and GMIL-4 administration group have the following compositions.

FS36 administration group: RPMI1640 supplemented with 10% FBS containing Flt-3 ligand (20 ng/ml), stem cell factor (SCF)(10 ng/ml), IL-3 (10 ng/ml), and IL-6 (10 ng/ml) (abbreviated as FS36).

GMIL-4 administration group: RPMI1640 supplemented with 10% FBS containing GM-CSF (20 ng/ml) and IL-4 (20 ng/ml).

GMSCF administration group: RPMI1640 supplemented with 10% FBS containing GM-CSF (20 ng/ml) and SCF (10 ng/ml).

In Examples 3, 6, and 7 described below and in the drawings related to these Examples, the GMIL-4 administration group (1), GMIL-4 administration group (2), GMSCF administration group, 0.1 GMSCF administration group, and 0.01 GMSCF administration group have the following compositions.

GMIL-4 administration group (1): IMDM supplemented with 10% FBS containing recombinant human GM-CSF (25 ng/ml) (Wako, Japan) and recombinant human IL-4 (50 ng/ml) (Wako, Japan).

GMIL-4 administration group (2): IMDM supplemented with 10% FBS containing recombinant human GM-CSF (100 ng/ml) (Wako, Japan) and recombinant human IL-4 (50 ng/ml) (Wako, Japan).

GMSCF administration group: IMDM supplemented with 10% FBS containing recombinant human GM-CSF (100 ng/ml) (Wako, Japan) and recombinant human SCF (50 ng/ml) (Wako, Japan).

0.1 GMSCF administration group: IMDM supplemented with 10% FBS containing recombinant human GM-CSF (10 ng/ml) (Wako, Japan) and recombinant human SCF (5 ng/ml) (Wako, Japan).

0.01 GMSCF administration group: IMDM supplemented with 10% FBS containing recombinant human GM-CSF (1 ng/ml) (Wako, Japan) and recombinant human SCF (0.5 ng/ml) (Wako, Japan).

In Example 6 described below and in the drawings related to this Example, (1) iDC treatment, (2) SeV/dF treatment, and (3) LPS treatment indicate the following treatments.

(1) iDC treatment: two days of incubation in a medium with the following concentration:

IMDM supplemented with 10% FBS.

(2) SeV/dF treatment: two days of incubation in a medium with the following concentration:

IMDM supplemented with 10% FBS containing F gene-deficient Sendai virus (moi=50).

(3) LPS treatment: two days of incubation in a medium with the following concentration:

IMDM supplemented with 10% FBS containing LPS (1 µg/ml).

LPS (SIGMA catalog No. L7895-1MG; source organism: *Salmonella typhosa*) was used in this experiment.

(4) Poly(I:C) treatment: two days of incubation in a medium with the following concentration:

IMDM supplemented with 10% FBS containing Poly(I:C) (100 µg/ml).

(5) CpG treatment: two days of incubation in a medium with the following concentration:

IMDM supplemented with 10% FBS containing CpG (10 µg/ml).

(6) R-848 treatment: two days of incubation in a medium with the following concentration:

IMDM supplemented with 10% FBS containing R-848 (1 µg/ml).

(7) OK432 treatment: two days of incubation in a medium with the following concentration:

IMDM supplemented with 10% FBS containing OK432 (0.5 KE/ml) (Chugai Pharmaceutical Co.; Japan Standard Commodity Classification No. 874299).

Example 1

Figure 1:
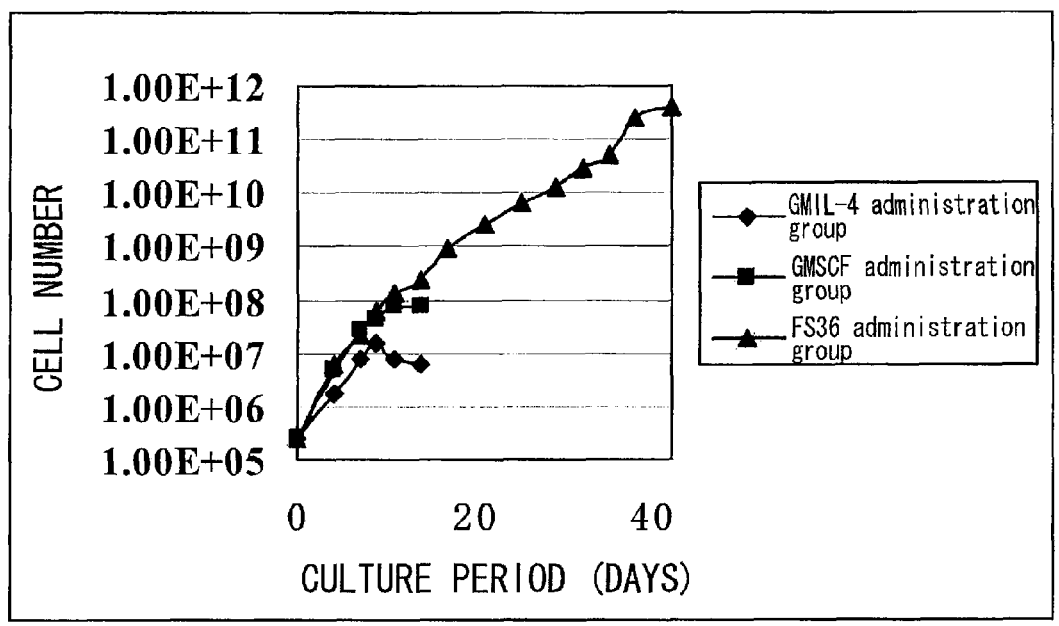
FIG. 1 shows growth curves of DC precursor cells cultured under the condition of the FS36 administration group, GMSCF administration group, or GMIL-4 administration group. Under the condition of the FS36 administration group, the cells were cultured for 42 days.

Assessment for Cytokine-Induced Expansion and Differentiation of Dendritic Cell (DC) Precursor Cells First, hematopoietic precursor cells were collected from the bone marrow of mouse (C3H) femur and tibia by negative selection (SpinSep mouse hematopoietic progenitor enrichment kit, StemCell technologies, Canada). The precursor cells were divided into three groups: FS36 administration group, GMIL-4 administration group, and GMSCF administration group. Then, the cells were cultured. The culture was started with $2.4 \times 10^5$ cells. The cells were passaged every three or four days to have a concentration of $2 \times 10^6$ cells/ml or lower, and the culture was continued for up to six weeks. Dendritic cell (DC) precursor cells were prepared in this process (FIG. 1). During this time, cells were counted to determine the growth rate. In addition, the differentiation ability of the above precursor cells was verified by FACS analysis after staining with anti-CD11b-FITC, anti-CD11c-PE, anti-c-kit-PE, and anti-CD131-PE (FIG. 3).

Figure 2:
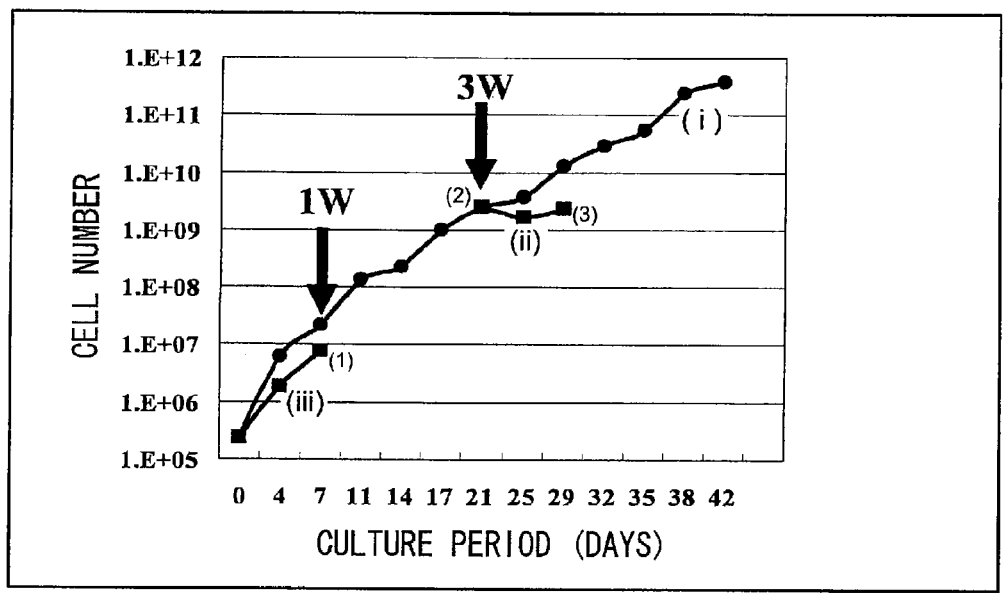
FIG. 2 shows a growth curve illustrating the process of preparing DCs under the conditions of (i) to (iii) described below, and photographs showing the morphologies of DCs and DC precursor cells at the time points of (1), (2), and (3). Dendrites were observed ((3)) at the time points of (1) and (3). Each of the DCs was prepared by one of the following steps.
Figure 2:
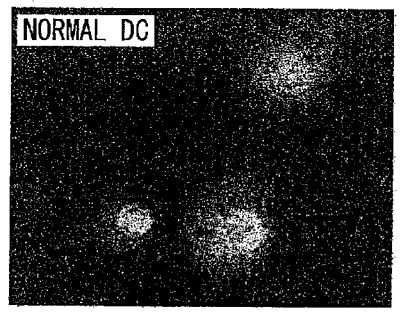
Figure 2:
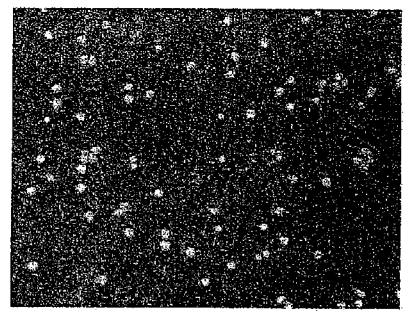
Figure 2:
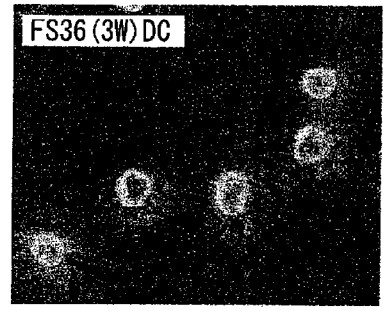

Mouse hematopoietic precursor cells were markedly expanded in the FS36 administration group as compared to the other administration groups, so that the cells were amplified about 10,000 times in 21 days by culturing using FS36 (FIGS. 1 and 2). The photograph shown as (1) in FIG. 2 corresponds to the time point indicated as (1) in the graph, and shows the cell morphology of DCs (observed under a microscope) obtained by culturing mouse hematopoietic precursor cells for seven days under the condition of the GMIL-4 administration group. The "normal DCs" in Examples 1, 2, 4, and 5 and in the drawings related to these Examples refers to these cells, i.e., DCs obtained by culturing mouse hematopoietic precursor cells for seven days under the condition of the GMIL-4 administration group. Dendrites can also be observed in the normal DCs. Furthermore, FIG. 2(3) shows a photograph of the cell morphology of DCs (observed under a microscope) obtained after four weeks of culture under the condition of the FS36 administration group shown in FIG. 8 followed by one week of culture under the medium condition of the GMIL-4 administration group. The cells were confirmed to have dendrites. The photograph shown as (3) in FIG. 2 was obtained in the process corresponding to curve (ii).

In the FS36 administration group, by culturing mouse hematopoietic precursor cells, the precursor cells which maintain the ability to differentiate into cells that become positive for the dendritic cell marker CD11c when subsequently cultured for one week in the presence of GM-CSF and IL-4, or the like were expanded. Mouse hematopoietic precursor cells were expanded about 10,000 times in 21 days of culture using FS36 (FIGS. 1 and 2). The number of CD11b$^+$ CD11c$^+$ cells in DCs obtained by differentiating the above-described cells using GM-CSF and IL-4, or GM-CSF and SCF was about 470 times greater than when differentiation was started immediately after cell collection.

Expansion was continued over six weeks (FIG. 1); however, the differentiation ability was gradually reduced after four weeks of expansion. The number of CD11c-positive cells after differentiation rapidly dropped after five weeks of expansion. Thus, it was revealed that a large number of CD11c-positive cells could be obtained by three weeks of expansion followed by one week of differentiation, or by four weeks of expansion followed by one week of differentiation (FIG. 10).

Furthermore, FIGS. 4 to 9 show growth curves of DC precursor cells resulting from one week of culturing mouse hematopoietic precursor cells under the conditions of the FS36 administration group, GMIL-4 administration group, and GMSCF administration group, and results of assessment for the cell differentiation using anti-CD11b-FITC and anti-CD11c-PE. The CD11b$^+$/CD11c$^+$ ratio (%) is shown in each figure. The culture method is as follows: about $10^6$ cells were removed weekly from mouse bone marrow hematopoietic precursor cells expanded by culture under the condition of the FS36 administration group, and then cultured for seven days under the condition of the GMIL-4 administration group or GMSCF administration group. After differentiation was confirmed by FACS analysis using anti-CD11b-FITC and anti-CD11c-PE, the cell differentiation efficiency was determined based on the CD11b$^+$/CD11c$^+$ ratio. The condition that gave the highest CD11b$^+$/CD11c$^+$ ratio was three weeks of culture under the condition of the FS36 administration group, followed by one week of culture under the medium condition of the GMIL-4 administration group, as shown in FIG. 7. Herein, the highest ratio of CD11b$^+$/CD11c$^+$ means that the proportion of DC precursor cells that differentiated into DCs is high. Meanwhile, FIG. 2(3) shows a photograph of the cell morphology of DCs (observed under a microscope) obtained by four weeks of culture under the condition of the FS36 administration group, followed by one week culture under the medium condition of the GMIL-4 administration group, as shown in FIG. 7. The cells were demonstrated to have dendrites.

Example 2

Differentiation of DC

DCs obtained from mouse hematopoietic precursor cells were infected with F gene-deficient Sendai virus (SeV/dF) at an moi of 50. Alternatively, LPS (1 μg/ml) was added to the DCs. Then, the cells were cultured for two days, and analyzed for the expression of DC surface markers with a flow cytometer using CD80-PerCP, CD86-PerCP, MHC classII-PerCP, and CD40-PerCP (FIGS. 11 and 12). The result showed that like normal DCs (FIG. 11(B)), when infected with Sendai virus or treated with LPS, DCs produced by one week of culture under the medium condition of the GMIL-4 administration group following three weeks of culture under the condition of the FS36 administration group expressed the co-stimulatory molecules CD80 and CD86, MHC Class II, and adhesion molecule (CD40) (FIG. 11(A)).

Example 3

Expansion of DCs by GM-CSF and SCF

Human cord blood CD34$^+$ cells (purchased from Cambrex) were expanded and differentiated by 35 days of culture under the condition of the GMSCF administration group or GMIL-4 administration group (1). During the culture period, the expression of c-kit, CD11c, and CD86 was analyzed using a flow cytometer every three to seven days of culture. When $1 \times 10^5$ human cord blood CD34$^+$ cells were cultured in a medium added with GM-CSF and SCF, CD11c$^+$ cells grew gradually and $3.8 \times 10^9$ cells were obtained after 35 days. Moreover, LPS was added on day 32, and FACS was carried out three days later using CD11c-PE and CD86-PE. The result showed that the expression of CD86 was enhanced by LPS (FIG. 16), similarly to the result described above in Example 2. Thus, both mouse and human CD11c$^+$ cells can be expanded by using cytokine cocktails (FIGS. 13, 14, and 15).

Example 4

Assessment of Expanded DCs for Cytokine Productivity, Antigen Uptake Ability, and T Cell Proliferation/Activation Ability DCs obtained by culture under the condition of FS36 administration group, followed by one week of culture under the medium condition of the GMIL-4 administration group, were assessed for cytokine productivity (FIG. 17), antigen uptake ability (FIG. 18), and T cell proliferation/activation ability (FIG. 19).

Similarly to normal DCs (obtained by culturing mouse hematopoietic precursor cells under the condition of the GMIL-4 administration group for seven days), DCs obtained from mouse bone marrow-derived hematopoietic precursor cells by three weeks of culture under the condition of the FS36 administration group, followed by one week of culture under the medium condition of the GMIL-4 administration group, were demonstrated to produce IL-12 and IFN-β (FIG. 17), and to have antigen uptake ability (FIG. 18) and T cell proliferation/activation ability (FIG. 19).

Example 5

Suppression of Lung Metastasis of Mouse Osteosarcoma by Administration of Expanded DCs <Sample Preparation>

Tumor lysate (containing $3 \times 10^5$ tumor cells) was added to mouse hematopoietic precursor cell-derived DCs ($1 \times 10^5$ cells) and incubated for eight hours. Then, F gene-deficient Sendai virus (SeV/dF) (moi=50) was introduced into the DCs, and the cells were further cultured for two days. The DCs after culture were administered to the caudal vein of mice (C3H; 7 week old female mice). Two days after administration, LM8 mouse osteosarcoma cells were administered to the caudal vein of mice. Seventeen days after administration of LM8 mouse osteosarcoma cells, the mice were thoracotomized and the number of metastatic nodules in the lung was counted with the naked eye (FIG. 20).

<Results>

As with normal DCs (obtained by culturing mouse hematopoietic precursor cells for seven days under the condition of the GMIL-4 administration group), cancer metastasis to the lung was confirmed to be suppressed with the administration of DCs obtained by culture under the condition of the FS36 administration group, followed by one week of culture under the condition of the GMIL-4 administration group or GMSCF administration group (see FIG. 20 (3) and (4)). This suggests that DCs obtained by culture under the condition of the FS36 administration group, followed by one week of culture under the medium condition of the GMIL-4 administration group or GMSCF administration group, are useful in cancer therapy.

Example 6

Expansion of DCs from Human-Derived Dendritic Cell Precursor Cells by GM-CSF and SCF (Part 1)

<Experiment 1>

Human cord blood-derived $CD34^+$ cells (purchased from Lonza) and human G-CSF-treated peripheral blood-derived $CD34^+$ cells (purchased from Lonza) were cultured in a medium containing GM-CSF and SCF for 35 days for expansion and differentiation.

<Results of Experiment 1>

The results shown in FIGS. 21(A) and (B) demonstrate that by culturing in a medium added with GM-CSF and SCF, a large number of cells were obtained from culture of cord blood-derived $CD34^+$ cells and culture of human G-CSF-treated peripheral blood-derived $CD34^+$ cells (FIGS. 21 and 22). The proportion of CD11c positive (+) cells was high in these cells (FIGS. 21(C) and (D), and FIG. 22(B)).

In the GMSCF administration group shown in the figure, cells at day 35 of culture and treated with LPS as described above were confirmed to have dendrites (FIG. 23).

<Experiment 2>

During the culture period of human cord blood-derived $CD34^+$ cells described in Experiment 1, the expression of CD11b, CD33, and HLA-ABC was analyzed using a flow cytometer for CD positive (+) cells at days 14 and 35 of culture (FIG. 24). Mature dendritic cells tend to be CD11c positive (+) and CD11b positive (+); CD11c positive (+) and CD33 positive (+); CD11c positive (+) and HLA-ABC positive (+).

Furthermore, during the culture period of human cord blood-derived $CD34^+$ cells, the expression of ICAM-1, CD86, HLA-DR, CD40, CD80, and CCR7 in cells at day 35 of culture when cells were treated with LPS or SeV/dF was analyzed using a flow cytometer (FIG. 25). When treated with LPS or SeV/dF, mature dendritic cells tend to show enhanced expression of ICAM-1, CD86, HLA-DR, CD40, CD80, and CCR7 as compared to when they are untreated (iDC treatment) (Nauta A J., et al. Mesenchymal stem cells inhibit generation and function of both CD34+-derived and monocyte-derived dendritic cells. J Immunol 177(4), 2080-2087 (2006); Yoneyama, Y., et al. Development of immunostimulatory virotherapy using non-transmissible Sendai virus-activated dendritic cells. Biochem Biophys Res Commun 355, 129-135 (2007)).

<Results of Experiment 2>

The results shown in FIG. 24 (see the arrows in the figure) showed the following tendency: CD11c positive (+) and CD11b positive (+); CD11c positive (+) and CD33 positive (+); and CD11c positive (+) and HLA-ABC positive (+).

Furthermore, according to the result shown in FIG. 25, the expression of ICAM-1, CD86, HLA-DR, CD40, CD80, and CCR7 tends to be enhanced with LPS or SeV/dF treatment as compared to without the treatment (iDC treatment).

Thus, based on the results shown in FIGS. 24 and 25, the tendency of the expression of surface markers suggests the possibility that the cells cultured and expanded in the medium containing GM-CSF and SCF are dendritic cells.

<Experiment 3>

During the culture period of human cord blood derived $CD34^+$ cells, cells at day 35 of culture were assessed for their phagocytotic ability (FIG. 26).

<Results of Experiment 3>

The phagocytotic ability of the cells was revealed to be enhanced at the 37° C. condition as compared to the 4° C. condition where the phagocytotic ability of the cells was very low (FIG. 26).

Furthermore, at 37° C., the phagocytotic ability of the cells was revealed to be reduced when the cells were treated with LPS as compared to with iDC. The known fact that the phagocytotic ability of dendritic cells is reduced as they mature (Yoneyama, Y., et al. Development of immunostimulatory virotherapy using non-transmissible Sendai virus-activated dendritic cells. Biochem Biophys Res Commun 355, 129-135 (2007)) suggests the possibility that the cells used in this experiment (cells cultured and expanded in a medium containing GM-CSF and SCF) are dendritic cells.

<Experiment 4>

During the culture period of human cord blood-derived CD34+ cells, cells at day 35 of culture were assessed for cytokine productivity. Human Inflammation kit (Catalog No. 551811) from Beckton Dickinson and company (BD) was used in this experiment (FIG. 27).

<Results of Experiment 4>

The productivity for IL-6, TNF-α, and IL-1β was enhanced by stimulation with LPS or such. The cells cultured and expanded in a medium containing GM-CSF and SCF are considered to have the ability to produce cytokines (FIG. 27).

<Experiment 5>

The ability to stimulate lymphocyte proliferation was assessed (FIG. 28). DCs obtained by culturing human cord blood-derived CD34+ cells in GMSCF medium were treated with mitomycin C (MMC), and then combined with CD3+ T cells at the following ratios.

Mixture Group 1:
Number of MMC-treated DCs: number of CD3+ T cells=1:100

Mixture Group 2:
Number of MMC-treated DCs: number of CD3+ T cells=1:10

The combined cells described above were cultured for five days. T cell proliferation was measured for Mixture group 2.

<Results of Experiment 5>

The effect produced by LPS stimulation or such was demonstrated to be stronger in Mixture group 2 as compared to Mixture group 1 (FIG. 28). In addition, the DCs described above were revealed to have the ability to proliferate/activate T cells (FIG. 28).

Thus, based on the results of Experiments 1 to 5, cells obtained by culturing human cord blood-derived CD34+ cells under the condition of the GMSCF administration group were confirmed to be mature dendritic cells.

The results described above show that the obtained cells form typical dendrites upon stimulation; express MHC Class II molecules, adhesion molecules, and co-stimulatory molecules; express inflammatory cytokines (including IL-6, TNF-α, and IL-1β; and have the endocytic activity and allostimulatory activity. Specifically, the results of Experiments 2 to 5 suggest that cells obtained by culture under the condition of the GMSCF administration group shown in Experiment 1 are thought to be biological active dendritic cells. Consequently, it was revealed that dendritic cells could be produced from dendritic cell precursor cells using a medium containing GM-CSF and SCF.

Example 7

Expansion of DCs from Human-Derived Cells by GM-CSF and SCF (Part 2)

FIG. 29 shows the effect of GM-CSF/SCF concentration on DC proliferation. Even when the concentrations of GM-CSF (100 ng/ml) and SCF (50 ng/ml) were reduced to 1/10 (10 ng/ml GM-CSF and 5 ng/ml SCF), high proliferation was maintained despite a slight reduction in cell count. Furthermore, DC expansion could be achieved even when the concentrations of GM-CSF (100 ng/ml) and SCF (50 ng/ml) were decreased to 1/100 (1 ng/ml GM-CSF and 0.5 ng/ml SCF). The percentage of CD11c positive cells at day 35 of culture is shown in FIG. 30. All of the administration groups yielded a high percentage of CD11c positive cells.

The data presented in FIGS. 29 and 30 show that to efficiently expand DCs, it is preferable to use GM-CSF and SCF at concentrations higher than 1 ng/ml and 0.5 ng/ml, respectively. Furthermore, since DCs can be expanded even when cultured under the condition of 0.01 GMSCF administration group, it is suggested that DCs can be efficiently expanded with a small amount of cytokine. Thus, the methods of the present invention are expected to be cost-effective methods for producing DCs.

INDUSTRIAL APPLICABILITY

The present invention enables production of large quantities of dendritic cells. The produced DCs can be made to present cancer antigens for use as anti-tumor DC vaccine. By using the methods of the present invention, it has become possible to efficiently produce a large quantity of DCs even when the number of DC precursor cells obtained from a patient is small. DCs obtained by these production methods have a strong anti-tumor effect, and thus can be used as DC vaccine which is useful in immunotherapy for cancer, infection, and the like. The present invention is expected to contribute greatly to immunotherapy against cancer.

The invention claimed is:

1. A method for producing a dendritic cell, wherein the method comprises the step of simultaneously culturing a primate dendritic cell precursor cell selected from the group consisting of a CD34+ cell and a monocyte in the presence of 1 ng/ml or higher concentration of granulocyte/macrophage colony stimulating factor (GM-CSF) and 0.5 ng/ml or higher concentration of stem cell factor (SCF) thereby expanding said dendritic precursor cells, wherein GM-CSF and SCF are the only cytokines supplemented to the culture medium.

2. The method of claim 1, wherein the dendritic cell precursor cell is a cell derived from human.

3. The method of claim 1, wherein the step is a step of simultaneously culturing a dendritic cell precursor cell in the presence of 10 ng/ml or higher concentration of granulocyte/macrophage colony stimulating factor (GM-CSF) and 5 ng/ml or higher concentration of stem cell factor (SCF).

4. The method of claim 1, wherein the step is a step of simultaneously culturing a dendritic cell precursor cell in the presence of 1 ng/ml to 100 ng/ml granulocyte/macrophage colony stimulating factor (GM-CSF) and 0.5 ng/ml to 50 ng/ml stem cell factor (SCF).

5. The method of claim 1, wherein the culturing step is carried on for three to six weeks.

6. The method of claim 5, wherein the culturing step is carried on for four to six weeks.

7. The method of claim 1, wherein the dendritic cell precursor cell is a CD34+ cell.

8. The method of claim 1, wherein the dendritic cell precursor cell is a monocyte.

* * * * *